(12) United States Patent
Gilley et al.

(10) Patent No.: US 8,001,472 B2
(45) Date of Patent: Aug. 16, 2011

(54) SYSTEMS AND METHODS FOR PROVIDING AUDIO AND VISUAL CUES VIA A PORTABLE ELECTRONIC DEVICE

(75) Inventors: Glenn Gregory Gilley, Los Altos, CA (US); Sarah A. Brody, Santa Clara, CA (US); Randall Hayes Ubillos, Los Altos, CA (US); Mihnea Calin Pacurariu, Los Gatos, CA (US); Jesse Lee Dorogusker, Los Altos, CA (US); Robert Edward Borchers, Pleasanton, CA (US); Donald Ginsburg, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 651 days.

(21) Appl. No.: 11/729,133

(22) Filed: Mar. 27, 2007

(65) Prior Publication Data
US 2008/0077620 A1 Mar. 27, 2008

Related U.S. Application Data

(60) Provisional application No. 60/846,414, filed on Sep. 21, 2006.

(51) Int. Cl.
*G09G 5/00* (2006.01)
*G06F 3/00* (2006.01)
*A63B 71/00* (2006.01)
*A63B 21/00* (2006.01)
*H04N 7/173* (2006.01)

(52) U.S. Cl. .............. 715/716; 715/834; 482/8; 482/9; 725/87

(58) Field of Classification Search ............ 715/716, 715/834; 482/8, 9; 725/87
See application file for complete search history.

(56) References Cited

U.S. PATENT DOCUMENTS

| | | | |
|---|---|---|---|
| 3,675,640 A | 7/1972 | Gatts | |
| 4,649,552 A | 3/1987 | Yukawa | |
| 5,379,057 A | 1/1995 | Clough et al. | |
| 5,412,564 A | 5/1995 | Ecer | |

(Continued)

FOREIGN PATENT DOCUMENTS
EP 1512370 3/2005
(Continued)

OTHER PUBLICATIONS

Oliver et al., Enhancing Exercise Performance through Real-time Physiological Monitoring and Music: A User Study, 2007, Pervasive Health Conference and Workshops, p. 1-10.*

(Continued)

*Primary Examiner* — Chat Do
*Assistant Examiner* — Jordany Núñez
(74) *Attorney, Agent, or Firm* — Kramer Levin Naftalis & Frankel LLP

(57) ABSTRACT

Methods and systems for providing a lifestyle companion system are provided. The lifestyle companion system can provide a platform to conduct a user interview. Based on the user interview responses, the system can suggest activities, references, and/or plug-in modules. During performance of activities, the system can provide audio and/or visual cues related to the activities and collect data indicative of the user's performance. Based on the collected data, the system can dynamically adapt the user's goals and/or activities the user is performing or will perform. In some embodiments of the present invention, the lifestyle companion system of the present invention can be applied to fitness, nutrition, and/or medical modules. The system also can be used to facilitate synchronous group activities.

32 Claims, 26 Drawing Sheets

U.S. PATENT DOCUMENTS

| | | | |
|---|---|---|---|
| 5,434,913 | A | 7/1995 | Tung et al. |
| 5,452,435 | A | 9/1995 | Malouf et al. |
| 5,471,405 | A | 11/1995 | Marsh |
| 5,490,247 | A | 2/1996 | Tung et al. |
| 5,673,691 | A | 10/1997 | Abrams et al. |
| 5,675,362 | A | 10/1997 | Clough et al. |
| 5,794,018 | A | 8/1998 | Vrvilo et al. |
| 5,819,735 | A | 10/1998 | Mansfield et al. |
| 5,857,939 | A | 1/1999 | Kaufman |
| 5,859,979 | A | 1/1999 | Tung et al. |
| 5,890,997 | A | 4/1999 | Roth |
| 5,913,062 | A | 6/1999 | Vrvilo et al. |
| 5,976,083 | A | 11/1999 | Richardson |
| 6,013,007 | A | 1/2000 | Root et al. |
| 6,032,108 | A | 2/2000 | Seiple et al. |
| 6,077,193 | A | 6/2000 | Buhler et al. |
| 6,135,951 | A | 10/2000 | Richardson et al. |
| 6,357,147 | B1 | 3/2002 | Darley et al. |
| 6,463,385 | B1 | 10/2002 | Fry |
| 6,527,674 | B1 | 3/2003 | Clem |
| 6,539,336 | B1 | 3/2003 | Vock et al. |
| 6,553,037 | B1 | 4/2003 | Pivowar et al. |
| 6,560,903 | B1 | 5/2003 | Darley |
| 6,582,342 | B2 | 6/2003 | Kaufman |
| 6,585,622 | B1 | 7/2003 | Shum et al. |
| 6,587,127 | B1 | 7/2003 | Leeke et al. |
| 6,619,835 | B2 | 9/2003 | Kita |
| 6,623,427 | B2 | 9/2003 | Mandigo |
| 6,702,719 | B1 | 3/2004 | Brown et al. |
| 6,716,139 | B1 | 4/2004 | Hosseinzadeh-Dolkhani et al. |
| 6,725,281 | B1 | 4/2004 | Zintel et al. |
| 6,749,537 | B1 | 6/2004 | Hickman |
| 6,790,178 | B1 | 9/2004 | Mault et al. |
| 6,793,607 | B2 | 9/2004 | Neil |
| 6,808,473 | B2 | 10/2004 | Hisano et al. |
| 6,898,550 | B1 | 5/2005 | Blackadar et al. |
| 6,910,068 | B2 | 6/2005 | Zintel et al. |
| 6,945,911 | B2 | 9/2005 | Jackowski |
| 7,030,735 | B2 | 4/2006 | Chen |
| 7,062,225 | B2 | 6/2006 | White |
| 7,070,539 | B2 | 7/2006 | Brown et al. |
| 7,085,590 | B2 | 8/2006 | Kennedy et al. |
| 7,171,331 | B2 | 1/2007 | Vock et al. |
| 7,174,227 | B2 | 2/2007 | Kobayashi et al. |
| 7,192,387 | B2 | 3/2007 | Mendel |
| 7,200,517 | B2 | 4/2007 | Darley et al. |
| 7,228,168 | B2 | 6/2007 | Dardik et al. |
| 7,251,454 | B2 | 7/2007 | White |
| 7,254,516 | B2 | 8/2007 | Case, Jr. et al. |
| 7,261,690 | B2 * | 8/2007 | Teller et al. .................... 600/300 |
| 7,277,726 | B2 | 10/2007 | Ahya et al. |
| 7,278,966 | B2 | 10/2007 | Hjelt et al. |
| 7,292,867 | B2 | 11/2007 | Werner et al. |
| 7,328,239 | B1 | 2/2008 | Berberian et al. |
| 7,353,139 | B1 | 4/2008 | Burrell et al. |
| 7,424,718 | B2 | 9/2008 | Dutton |
| 7,454,002 | B1 | 11/2008 | Gardner et al. |
| 7,496,277 | B2 | 2/2009 | Ackley et al. |
| 7,519,327 | B2 | 4/2009 | White |
| 7,523,040 | B2 * | 4/2009 | Kirchhoff et al. ................. 705/1 |
| 7,526,524 | B2 | 4/2009 | White |
| 7,591,760 | B2 | 9/2009 | Gordon et al. |
| 7,603,255 | B2 * | 10/2009 | Case et al. .................... 702/182 |
| 7,618,345 | B2 | 11/2009 | Corbalis et al. |
| 7,636,754 | B2 | 12/2009 | Zhu et al. |
| 7,656,824 | B2 | 2/2010 | Wang et al. |
| 7,670,263 | B2 | 3/2010 | Ellis et al. |
| 7,683,252 | B2 * | 3/2010 | Oliver et al. .................... 84/612 |
| 2001/0054180 | A1 | 12/2001 | Atkinson |
| 2002/0007313 | A1 | 1/2002 | Mai et al. |
| 2002/0022774 | A1 | 2/2002 | Karnieli |
| 2002/0077784 | A1 | 6/2002 | Vock et al. |
| 2002/0095460 | A1 | 7/2002 | Benson |
| 2003/0017914 | A1 | 1/2003 | Jackowski |
| 2003/0028116 | A1 | 2/2003 | Birnbaum |
| 2003/0059747 | A1 | 3/2003 | Yoshida et al. |
| 2003/0097878 | A1 | 5/2003 | Farringdon et al. |
| 2003/0175666 | A1 | 9/2003 | Tanabe et al. |
| 2003/0208113 | A1 | 11/2003 | Mault et al. |
| 2003/0220971 | A1 | 11/2003 | Kressin |
| 2003/0224337 | A1 | 12/2003 | Shum et al. |
| 2003/0229900 | A1 | 12/2003 | Reisman |
| 2004/0002041 | A1 | 1/2004 | Peplinski et al. |
| 2004/0029684 | A1 | 2/2004 | Zarif |
| 2004/0091843 | A1 | 5/2004 | Albro et al. |
| 2004/0102931 | A1 | 5/2004 | Ellis et al. |
| 2004/0106449 | A1 | 6/2004 | Walker et al. |
| 2004/0107116 | A1 | 6/2004 | Brown |
| 2004/0143673 | A1 | 7/2004 | Kristjansson |
| 2004/0201595 | A1 | 10/2004 | Manchester |
| 2004/0220017 | A1 | 11/2004 | Gordon et al. |
| 2004/0229729 | A1 | 11/2004 | Albert et al. |
| 2005/0008993 | A1 | 1/2005 | Bergh et al. |
| 2005/0008994 | A1 | 1/2005 | Bisogno |
| 2005/0010638 | A1 | 1/2005 | Richardson et al. |
| 2005/0014113 | A1 | 1/2005 | Fleck et al. |
| 2005/0042582 | A1 | 2/2005 | Graves |
| 2005/0044503 | A1 | 2/2005 | Richardson et al. |
| 2005/0058970 | A1 | 3/2005 | Perlman et al. |
| 2005/0060368 | A1 | 3/2005 | Wang et al. |
| 2005/0101314 | A1 | 5/2005 | Levi |
| 2005/0107116 | A1 | 5/2005 | Yamaguchi |
| 2005/0107216 | A1 | 5/2005 | Lee et al. |
| 2005/0113649 | A1 | 5/2005 | Bergantino |
| 2005/0164833 | A1 | 7/2005 | Florio |
| 2005/0172311 | A1 | 8/2005 | Hjelt et al. |
| 2005/0176461 | A1 | 8/2005 | Bozzone et al. |
| 2005/0180341 | A1 | 8/2005 | Nelson et al. |
| 2005/0202934 | A1 | 9/2005 | Olrik et al. |
| 2005/0209050 | A1 | 9/2005 | Bartels |
| 2005/0227811 | A1 | 10/2005 | Shum et al. |
| 2005/0240705 | A1 | 10/2005 | Novotney et al. |
| 2005/0266385 | A1 | 12/2005 | Bisogno |
| 2005/0287499 | A1 | 12/2005 | Yeager |
| 2006/0035200 | A1 | 2/2006 | Pittman |
| 2006/0047208 | A1 | 3/2006 | Yoon |
| 2006/0063980 | A1 | 3/2006 | Hwang et al. |
| 2006/0085272 | A1 | 4/2006 | Case et al. |
| 2006/0107822 | A1 | 5/2006 | Bowen |
| 2006/0173972 | A1 | 8/2006 | Jung et al. |
| 2006/0197670 | A1 | 9/2006 | Breibart |
| 2006/0197753 | A1 | 9/2006 | Hotelling |
| 2006/0199155 | A1 | 9/2006 | Mosher |
| 2006/0205564 | A1 | 9/2006 | Peterson |
| 2006/0238517 | A1 | 10/2006 | King et al. |
| 2006/0250524 | A1 | 11/2006 | Roche |
| 2006/0253874 | A1 | 11/2006 | Stark et al. |
| 2006/0256130 | A1 | 11/2006 | Gonzalez |
| 2006/0263750 | A1 | 11/2006 | Gordon |
| 2007/0026999 | A1 | 2/2007 | Merolle et al. |
| 2007/0033068 | A1 | 2/2007 | Rao et al. |
| 2007/0059672 | A1 | 3/2007 | Shaw |
| 2007/0074619 | A1 * | 4/2007 | Vergo .............................. 84/612 |
| 2007/0110074 | A1 | 5/2007 | Bradley et al. |
| 2007/0130476 | A1 | 6/2007 | Mohanty |
| 2007/0135264 | A1 | 6/2007 | Rosenberg |
| 2007/0136093 | A1 * | 6/2007 | Rankin et al. ..................... 705/2 |
| 2007/0141540 | A1 | 6/2007 | Borg |
| 2007/0166683 | A1 | 7/2007 | Chang et al. |
| 2008/0096726 | A1 * | 4/2008 | Riley et al. ......................... 482/8 |
| 2008/0155470 | A1 | 6/2008 | Khedouri et al. |
| 2008/0177860 | A1 | 7/2008 | Khedouri et al. |
| 2009/0047645 | A1 | 2/2009 | Dibenedetto et al. |
| 2009/0087819 | A1 | 4/2009 | Adachi et al. |
| 2009/0312105 | A1 | 12/2009 | Koplar |

FOREIGN PATENT DOCUMENTS

| | | |
|---|---|---|
| EP | 1585014 | 10/2005 |
| GB | 2253706 | 9/1992 |
| GB | 2284060 | 5/1995 |
| GB | 2409040 | 6/2005 |
| JP | 2007013228 A | 1/2007 |
| WO | WO 97/14357 | 4/1997 |
| WO | WO02062425 A1 | 8/2002 |
| WO | 02/093272 | 11/2002 |
| WO | WO2005032363 A1 | 4/2005 |
| WO | WO2005036918 A1 | 4/2005 |

| | | |
|---|---|---|
| WO | WO 2005/082472 | 9/2005 |
| WO | WO2006042415 A1 | 4/2006 |
| WO | WO2007099206 A1 | 9/2007 |

OTHER PUBLICATIONS

Reinventing the Scroll Wheel, CNET news.com, Aug. 22, 2006: <http://www.news.com/2300-1041_3-6107951-1.html?tag=ne.gall.pg; http://www.news.com/2300-1041_3-6107951-2.html?tag=ne.gall.pg; http://www.news.com/2300-1041_3-6107951-3.html?tag=ne.gall.pg; http://www.news.com/2300-1041_3-6107951-4.html?tag=ne.gall.pg; http://www.news.com/2300-1041_3-6107951-5.html?tag=ne.gall.pg; http://www.news.com/2300-1041_3-6107951-6.html?tag=ne.gall.pg; http://www.news.com/2300-1041_3-6107951-7.html?tag=ne.gall.pg; and http://www.news.com/2300-1041_3-6107951-8.html?tag=ne.gall.pg>.

Microsoft Zune Impressions—Part 1, DigitalArts Online Magazine, Dec. 4, 2006: <http://www.digitalartsonline.co.uk/bloqs/index.cfm?entryid=184&blogid=2>.

Sensei.com, Feb. 10, 2008: <http://www.sensei.com/senseipublic/Inner.aspx>.

Podfitness Delivers On myMedia Promise, Utah Tech Jobs.com, Nov. 13, 2006: <http://utahtechjobs.com/index.php/2006/11/13/podfitness-delivers-on-mymedia-promise/>.

* cited by examiner

SYSTEMS AND METHODS FOR PROVIDING AUDIO AND VISUAL CUES VIA A PORTABLE ELECTRONIC DEVICE

CROSS-REFERENCE TO RELATED APPLICATIONS

This claims priority to U.S. Provisional Patent Application No. 60/846,414 to Gilley et al., filed on Sep. 21, 2006 (referred to below as "the incorporated provisional patent application"), the entirety of which is incorporated herein by reference.

This also is related to:

U.S. patent application Publication No. 2008-0086318 to Gilley et al., filed on Mar. 27, 2007, entitled "LIFESTYLE COMPANION SYSTEM," (referred to herein as "the incorporated LIFESTYLE COMPANION document"), the entirety of which is incorporated herein by reference;

U.S. patent application Publication No. 2008-0076637 to Gilley et al., filed on Mar. 27, 2007, entitled "DYNAMICALLY ADAPTIVE SCHEDULING SYSTEM," (referred to herein as "the incorporated ADAPTIVE SCHEDULING SYSTEM document"), the entirety of which is incorporated herein by reference;

U.S. patent application Publication No. 2008-0077619 to Gilley et al., filed on Mar. 27, 2007, entitled "SYSTEMS AND METHODS FOR FACILITATING GROUP ACTIVITIES," (referred to herein as "the incorporated GROUP ACTIVITIES document"), the entirety of which is incorporated herein by reference;

U.S. patent application Publication No. 2008-0077881 to Gilley et al., filed on Mar. 27, 2007, entitled "VARIABLE I/O INTERFACE FOR PORTABLE MEDIA DEVICE," (referred to herein as "the incorporated VARIABLE I/O document"), the entirety of which is incorporated herein by reference;

U.S. patent application Publication No. 2008-0077489 to Gilley et al., filed on Mar. 27, 2007, entitled "REWARDS SYSTEMS," (referred to herein as "the incorporated REWARDS SYSTEMS document"), the entirety of which is incorporated herein by reference; and U.S. patent application Publication No. 2008-0076972 to Dorogusker et al., filed on Mar. 27, 2007, entitled "INTEGRATED SENSORS FOR TRACKING PERFORMANCE METRICS," (referred to herein as "the incorporated INTEGRATED SENSORS document"), the entirety of which is incorporated herein by reference.

BACKGROUND OF THE INVENTION

The present invention can generally relate to a lifestyle companion system. More particularly, the present invention can relate to a system that coordinates multiple corridors of experiences in a person's life.

Conventional systems typically focus only on one aspect of a person's experiences. Conventional systems typically do not intelligently integrate multiple aspects of a person's experiences. For example, a typical piece of software may be implemented to measure a user's heart rate during an exercise routine. But, that software typically cannot coordinate the heart rate information to the user's general fitness goals, nor intelligently use that information to assist the user in reaching his goals.

Accordingly, it would be desirable to provide a system that can bridge numerous corridors of experiences in a person's life and coordinate them for maximum efficiency and enjoyment.

SUMMARY OF THE INVENTION

In accordance with one embodiment of the present invention, a lifestyle companion system can be provided for coordinating multiple corridors of a user's life. The lifestyle companion system can include devices and methods for providing a platform for conducting user interviews, suggesting activities and references based on interview responses, providing a platform for a user to schedule activities, collecting data about a user during performance of activities or throughout the user's day, and/or providing progress reports. The method also can include assigning user category levels (e.g., activity levels) based on interview responses. In some embodiments of the present invention, the lifestyle companion system can coordinate a user's fitness, nutrition, and medical experiences.

The lifestyle companion system can integrate user-selectable plug-in modules that are focused on specialized topics. For example, plug-in modules can be specialized for particular periods in a child's development, students, expectant parents, new parents, seniors, specific sports enthusiasts, food connoisseurs, geographical regions, health conditions, holidays, etc. Each module can have coordinating questionnaires, suggested activities, suggested references, instructions, logging tools, audiobooks, videos, podcasts and other types of activities or information tailored for the specialty of the module.

In one embodiment of the present invention, user data can be collected using a tracking device that stores the data itself or transmits the data to a local server, a central server, a server dedicated to storage of user profile information, or any combination thereof. Tracking devices can include passive tracking devices that require the user and/or another authorized entity to manually enter user data, active tracking devices having sensors that automatically gather data about the user and/or activities performed by the user, or any combination thereof. In one embodiment of the present invention, sensors of the active tracking devices can be attached to the user (e.g., in clothing or accessories) or disposed in equipment used by the user.

In one embodiment of the present invention, the tracking device also can provide a user interface for the user to, e.g., access the user's profile. Information stored in the user's profile can include medical information, the user's goals and progress towards the goals, reference information, activity information, the user's responses to the user interview, and any other information related to the user's interaction with the lifestyle companion system. Activity information can include, for example, media files and adjustable parameters associated with an activity.

In one embodiment of the present invention, media (e.g., audio and/or visual) cues can be provided to the user during the user's performance of activities. Audio and visual cues can include, for example, instructions for the activity, feedback on a user's progress, motivational feedback, and/or entertainment information. The media cues can be played at predetermined points during an activity, based on performance metrics, or at the initiation of the user. Visual cues can include graphical information (e.g., text, still images, and/or videos).

In one embodiment of the present invention, a user's short-term and/or long-term goals and activities can be dynamically adapted in response to data collected about the user. The data can include that collected during a user's performance of an activity (e.g., performance metrics), and/or collected about the user throughout the user's day.

In one embodiment of the present invention, the lifestyle companion system can be used to coordinate group activities. Each person in the group can be provided with a tracking device to facilitate their performance of predetermined group activities. A common activity file or complementary activity files can be loaded onto each of the tracking devices and, in one embodiment of the present invention, synchronized by a synchronization signal. Audio and visual cues can be provided to the users in response to each user's own performance metrics or the performance metrics of other group members. Data can be collected about each user's performance, individually and as a group. Responsive to such data, the lifestyle companions system can adjust current or future activities of each user and/or the group.

BRIEF DESCRIPTION OF THE DRAWINGS

The above and other advantages of the present invention will be apparent upon consideration of the following detailed description, taken in conjunction with accompanying drawings, in which like reference characters refer to like parts throughout, and in which:

FIG. 3 shows an illustrative graphic user interface of a fitness welcome screen in accordance with one embodiment of the present invention;

FIG. 5 shows an illustrative graphic user interface of a fitness interest screen in accordance with one embodiment of the present invention;

DETAILED DESCRIPTION OF THE INVENTION

The present invention can include a lifestyle companion system for coordinating multiple corridors of a user's life. The lifestyle companion system can intelligently recommend lifestyle choices and activities based on information and data collected about the user. As described in greater detail below with respect to FIG. 1, the lifestyle companion system can provide a platform for conducting user interviews, suggest activities and references based on interview responses, provide a platform for a user to schedule activities, collect data about a user during performance of activities or throughout the user's day, and/or provide progress reports. The system also can assign user category levels (e.g., activity levels) based on interview responses. Responsive to the data collected about the user, the lifestyle companion system can adjust or adapt a user's goals or activities.

Figure 1:
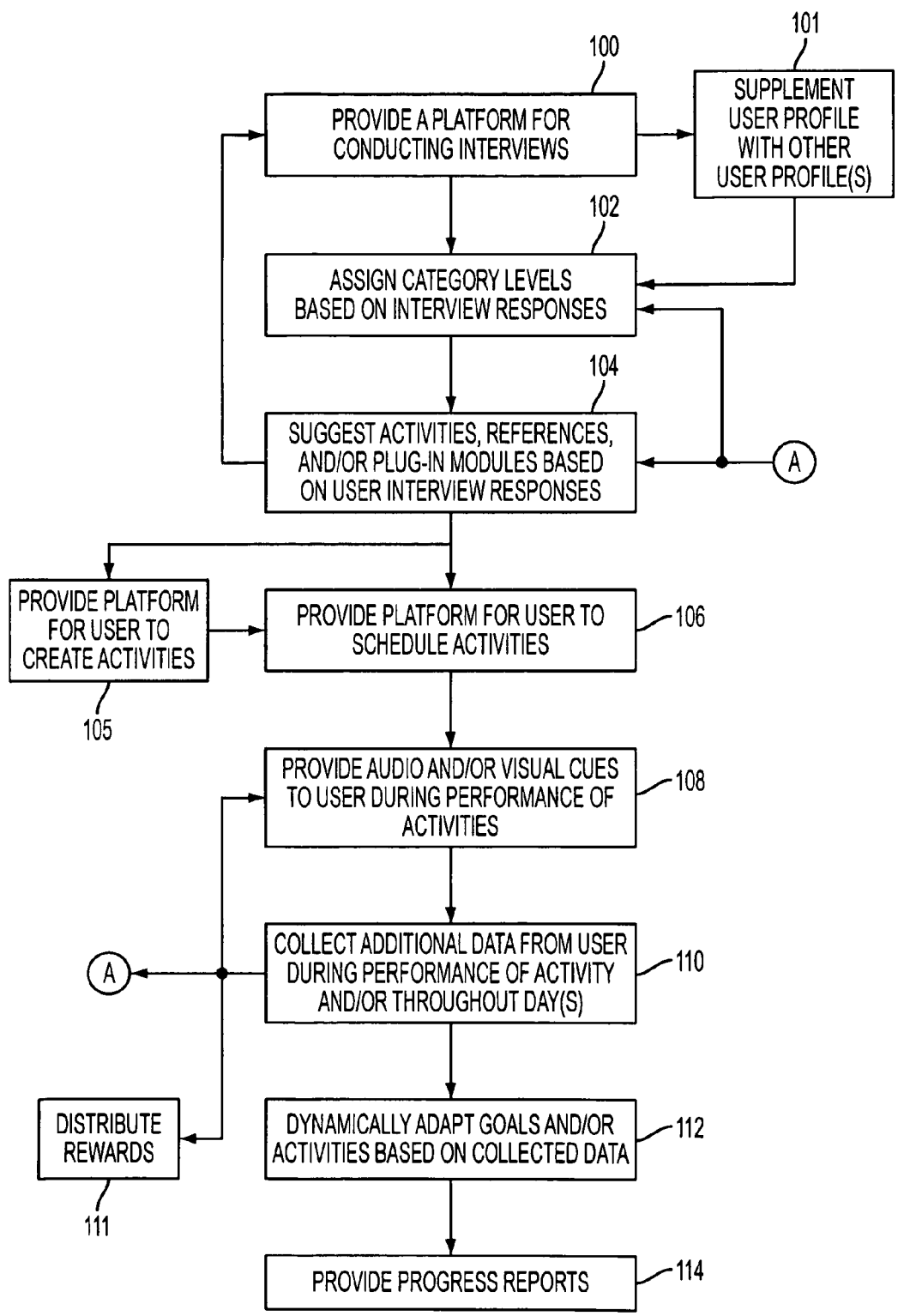
FIG. 1 illustrates a flowchart for implementing a lifestyle companion system in accordance with one embodiment of the present invention.

FIG. 1 illustrates a flowchart for implementing a lifestyle companion system in accordance with one embodiment of the present invention. In step 100, the lifestyle companion system can provide a platform for conducting user interviews.

In one embodiment of the present invention, the lifestyle companion system can request that the user input information about the user's physical and mental health. Physical health information can include information about the medications the user is taking, the user's physical limitations, illnesses, medical conditions (e.g., pregnancy), and/or risk factors. A health interview also can address nutrition, weight, breathing metrics (e.g., breaths per minute or some other related metric), relaxation and/or sleep. Interview questions about nutrition and weight can address weight goals and the user's current nutritional habits. Interview questions about illnesses and medical conditions can address, e.g., sexually transmitted diseases, allergies and sinus problems, asthma, arthritis, conditions related to the brain and nervous system, cancer, cerebral palsy, chronic diseases, chronic pain, diabetes, fatigue, fibromyalgia, headaches and migraines, heart disease and cardiovascular issues, infections, joints and muscle problems, liver conditions, multiple sclerosis, Parkinson's disease, respiratory conditions, surgery recovery, or any other medical condition.

Interview topics also can be gender or age specific. A women's health interview can address, for example, menopause, pregnancy, fertility, etc. A men's health interview can address, e.g., fertility, impotence, prostate concerns, etc. A children's health interview can be divided into sub-categories, e.g., issues related to infants and toddlers, children, and teenagers.

A mental health interview can address, for example, anxiety, caregiving and coping, depression, and/or drug & alcohol addiction.

The lifestyle companion system also can interview the user about non-health related topics, e.g., spirituality/religion, identity (e.g., sense of belonging), relationships, career, financial condition, environment, hobbies, interests, other personal information, and goals regarding the same. An identity (sense of belonging) interview may address, for example, the organizations to which the user belongs socially and/or professionally. A relationships interview can address, for example, the marital and/or familial status of the user. The relationship interview also can address the quality of the user's relationships with his/her family. A career interview can address, for example, the length of time the user has worked in the present job, the user's current occupational position, and/or the user's level of enjoyment of the user's occupation. A finance interview can address, for example, net wealth, credit situation, spending habits, etc. An environment interview can address, for example, the user's home, office, clothing, transportation, fitness memberships, access to exercise equipment, etc.

Once the user completes the user interview provided in step 100, the lifestyle companion system can establish a user profile for the user based on the user's interview responses. As the user's lifestyle changes (e.g., the user's goals change or the user's familial status changes), this profile can be updated by the user at a later date by changing responses to the interview questions. In response to updates to the user profile, the lifestyle companion system can alter the activities, references, and plug-in modules suggested (e.g., as described below with respect to step 104) and/or adapt the user's goals or scheduled activities (e.g., as described below with respect to step 112).

The user profile also can store user-associated information generated by the lifestyle companion system in later steps. For example, the user profile can store information related to categories to which the user is assigned in step 102, activities and references suggested by the lifestyle companion system in step 104, activities created by the user in step 105, data collected about the user in step 110, and/or rewards distributed to the user in step 111. The user profile can store information about activities in activity files. In one embodiment, an activity file can include, for example, adjustable parameters associated with an activity, media files associated with the activity for providing media cues to the user, and any other information related to the activity.

In step 101, the lifestyle companion system can supplement the user's profile with data from profiles of user-authorized entities (e.g., relatives, doctor, therapist, fitness trainer, etc.). For example, the user profile can be supplemented with data from the profiles of family members so that the lifestyle companion system can suggest medical activities (e.g., exams) and references in step 104 based on a more accurate profile of potential genetic health risks. The user's profile also can be supplemented with data from the profiles of workout partners so that the lifestyle companion system can suggest, for example, fitness activities that are appropriate for the user and his workout partners. The user's profile also can be supplemented with the profiles of dining partners so that the lifestyle companion system can suggest, for example, nutritional activities (e.g., recipes, restaurants, etc.) that are appropriate for the user and his dining partners. Illustrative nutrition-based applications of the present invention are described in greater detail with respect to FIG. 25.

As used herein, an entity is authorized by the user when the user has granted the entity permission to obtain information from the user's profile or transfer information into the user's profile. For example, user-authorized entities can include a family member, employer, physical therapist, psychologist, doctor, physical trainer, coach, etc.

In step 102, the lifestyle companion system can assign or associate certain categories to the user profile based on the user's responses to the interview. For example, based on the user's responses to fitness questions, the lifestyle companion system can assign an activity level to the user's profile, e.g., beginner, intermediate, or advanced. Based on the assigned activity level, the lifestyle companion system can later suggest fitness activities in step 104 that are more suited to the fitness category assigned to the user profile, and, thus, more suited to the capabilities of the user.

In step 104, the lifestyle companion system can suggest activities for the user based on the user's responses to the user interview, either directly or indirectly (e.g., based on the category level assigned in step 102). For example, if a user provides information about alcohol addiction in the interview, the lifestyle companion system can limit suggestions to activities that may be alcohol-related and/or provide suggestions to alternatives to alcohol-related activities. If a user indicates in the interview that he/she is a single parent, the lifestyle companion system can provide suggestions of activities to accommodate these circumstances, such as more nutritious "eating out" options instead of time-consuming home food preparation. If a user indicates in the interview that he is diabetic, the lifestyle companion system can suggest food choices that accommodate a low-sugar, low-carbohydrate diet. If a user inputs into the system that he/she has an asthma condition, the system can suggest hobbies or jobs in arid and pollution-free areas.

In step 104, the lifestyle companion system also can suggest references for the user to consult based directly or indirectly on the user's interview responses. For example, the lifestyle companion system can provide information and/or website links to specialized counselors, support groups, or specialized organizations that are tailored to the conditions indicated by the user's interview responses.

The lifestyle companion system can provide access to one or more of the suggested references via a personal webpage customized for the user. The personal webpage also can include a journal, blog, or secure data vault in which the user can store highly sensitive data that can be accessed, e.g., via the internet by any entity authorized by the user. The secure data vault can be compartmentalized by topics, e.g., medical and alternative therapy records, family health conditions, financial information, travel documents, etc. The personal webpage also can permit a user to store any other information in a data repository.

In step 104, the lifestyle companion system also can suggest plug-in modules based directly or indirectly on the user's interview responses. Plug-in modules can contain information tailored for a specialized topic. For example, the modules can be specialized for particular periods in a child's development, students, expectant parents, new parents, seniors, specific sports enthusiasts, food connoisseurs, geographical regions, health conditions, themed or seasonal projects, mental wellness, life satisfaction assessment and goal setting, etc.

In one embodiment of the present invention, plug-in modules can be co-branded by third parties (e.g., content partners). For example, for modules tailored to food connoisseurs, the information contained in the module can be provided and co-branded by the Food Network.

Each module can have coordinating questionnaires, suggested activities, suggested references, instructions, logging tools, podcasts and other types of activities or information tailored for the specialty of the module.

The suggested modules can be offered to a user free of charge or for purchase, e.g., from a media management and distribution server similar to that offered under the trademark iTunes™ by Apple Inc. of Cupertino, Calif.

Once a user selects desired plug-in modules, the modules can be installed into a user's lifestyle companion system. For those modules containing specialized questionnaires, the lifestyle companion system can return to step 100 to continue the user interview using the specialized questionnaire.

The lifestyle companion system also can be pre-loaded with one or more plug-in modules, permit a user to search for and download specific modules from a database, permit a user to directly identify and download a plug-in module offered by a user-authorized entity, and/or permit user-authorized entities to download modules into the user profile.

In one embodiment of the present invention, in step 104, the lifestyle companion system can provide a selection of activities, references, and plug-in modules from which the user can choose. That selection can themselves be selected from a predetermined list of activities, references, and plug-in modules provided or pre-approved by the user or a user-authorized entity.

In one embodiment of the present invention, the lifestyle companion system also can suggest activities, references, and/or plug-in modules based on other information stored in the user's profile, e.g., data the system collects about the user in step 110. For example, if the lifestyle companion system collects data about the user that indicates the user is in poor physical shape, the lifestyle companion can suggest less physically-active activities for the user in step 104, irrespective of the level of fitness the user indicates in the user interview of step 100. The lifestyle companion system also can suggest activities that a user has not performed over a predetermined amount of time or that a user has not performed satisfactorily, as indicated by the data previously collected in accordance with step 110.

In one embodiment of the present invention, the lifestyle companion system can suggest activities based on a pseudo-random protocol. The lifestyle companion system can randomly suggest activities within a certain category. For example, the system can randomly suggest fitness activities adapted to the same muscle group or type of exercise.

In one embodiment of the present invention, the lifestyle companion system can suggest activities based on the frequency in which the user has performed the activities. For example, the system can suggest activities that the user has not performed over a predetermined amount of time. The system also can suggest activities that the user frequently schedules based on the assumption that the user enjoys those activities more.

In one embodiment of the present invention, the lifestyle companion system can select suggested activities, references, and plug-in modules from a database. The database can be stored, for example, in a central server, local server, or a portable electronic device, as discussed in greater detail below with respect to FIG. 2.

In step 105, the lifestyle companion system can provide a platform for the user to create activities. This can include providing a platform for the user to download activities created by a third party into the user's profile. Third parties can include user-authorized entities (e.g., the user's doctor, personal fitness trainer, physical therapist, friend, family member, real estate agent, financial advisor, etc.) and/or companies that offer themed and/or branded activities or compilations thereof (e.g., gyms, television networks, diet plans, nutrition-oriented companies, etc.). The third party activities can be can be offered to a user free of charge or for purchase, e.g., from a media management and distribution server similar to iTunes™.

Activities created by the user also can include customizations of activities suggested by the lifestyle companion system in step 104, customizations of activities created by third parties, activities the user creates from scratch, or compilations of activities that are suggested, customized, or otherwise created by the user. In one embodiment of the present invention, the lifestyle companion system can permit a user to customize an activity by permitting the user to set the value of one or more adjustable parameters associated with the activity. Adjustable parameters of an activity are discussed in greater detail below. Once the user has completed creating activities, the user can share these activities with user-authorized entities, e.g., the user's doctor, trainer, physical therapist, friend, etc.

In step 106, the lifestyle companion system can provide a platform for the user to schedule one or more activities. The lifestyle companion system can permit the user to choose from the activities suggested in step 104 or created or downloaded by the user in step 105. Activities created or downloaded by the user can include activities that the user created or downloaded in step 105 or that the user has previously created or downloaded, e.g., from previous sessions with the lifestyle companion system.

In step 108, the lifestyle companion system can assist or motivate the user during performance of activities by providing audio and/or visual cues, individually or simultaneously, that are related to the activities. Audio and visual cues can include, for example, instructions for an activity, feedback on a user's progress, and/or motivational feedback. The cues can be pre-loaded or dynamically built based on a user's performance metrics, as determined from data collected in step 110. The media cues can be intelligently mixed with entertainment media (e.g., music or video) the user is playing during performance of a scheduled activity. Visual cues can include text, still images, and/or videos.

In one embodiment of the present invention, performance metrics can include metrics that track the amount or quality of a fitness activity that a user has performed, physiological metrics or rate of change thereof, or any combination thereof.

The media cues can be played at predetermined points during an activity, at unscheduled points during an activity based on performance metrics, or at the initiation of the user. For example, when data collected about the user's performance in step 110 indicates that a user has run his/her fastest mile, the lifestyle companion system can provide the user with audio and/or visual cues indicating that he has achieved a personal best and congratulating the user for reaching a particular performance metric. In one embodiment of the present invention, the congratulatory cue can be in the form of a predetermined song or a predetermined video that the user has earned through his performance.

In step 110, the lifestyle companion system can collect additional data about the user's performance of specific activities and/or throughout the user's day. User data can be collected using a tracking device that stores the data itself or transmits the data to a local server, a central server, a server dedicated to storage of user profile information, or any combination thereof. Tracking devices can include passive tracking devices that require the user and/or another authorized entity to manually enter user data, active tracking devices that automatically log data about the user and/or activities performed by the user, or any combination thereof.

Active tracking devices for use with the methods and systems according to the invention can include any electronic device coupled to or incorporating sensors that can capture information about a user, e.g., pedometers, devices having accelerometers, heart rate monitors, oximeters, location-tracking (e.g., GPS) devices, devices having temperature sensors, devices having heat flux sensors, electrocardiogram devices, scales, glucometer devices, devices having activity tracking sensors, any other suitable tracking device useful for capturing data about a person's activities, any other suitable tracking device useful for capturing data about a person's physical or mental state, or any combination thereof. In one embodiment of the present invention, the active tracking device can include a portable media device operatively coupled to sensors attached to the user (e.g., in clothing or accessories) or in equipment used by the user. The sensors and active tracking device also can be similar to those described in the incorporated INTEGRATED SENSORS document.

The data collected in step 110 can be stored and thereafter analyzed, for example, by analysis software, the user, or a user-authorized entity. The data collected in step 110 also can be used by the lifestyle companion systems in other steps of FIG. 1. For example, the lifestyle companion system can change the category level assigned to a user in step 102 based on the collected data. The lifestyle companion system also can use the collected data to suggest activities, references, and/or plug-in modules in step 104. The lifestyle companion system also can use the collected data to determine when to provide audio and/or visual cues to the user and the type or content of the cues, e.g., as described with respect to step 108. The lifestyle companion system also can use the collected data to dynamically adapt a user's goals and/or activities in step 112.

To motivate the user to perform the scheduled activities, the lifestyle companion system also can use the collected data to distribute rewards to the user in step 111, e.g., in accordance with the incorporated REWARDS SYSTEMS document and the incorporated provisional patent application. For example, the lifestyle companion system can distribute rewards to users based on the user's performance metrics (over a period of time or during a single activity). Rewards can include monetary rewards, rewards points that can be exchanged for merchandise or services, access to features or activities, or any other reward described in the incorporated REWARDS SYSTEMS document and the incorporated provisional patent application.

Data collected in step 110 also can be stored and shared with authorized entities, e.g., the user's personal fitness trainer, doctor, physical therapist, sports coach, etc.

In step 112, the lifestyle companion system can dynamically adapt the user's short-term or long-term goals based on the data collected in step 110. For example, if the collected data (e.g., sensor data) indicates that the user will not reach a target performance metric based on his performance during an individual workout (e.g., the number of calories burned), the lifestyle companion system can temporarily reduce the target performance metric to a level that is more attainable during the workout in order to maintain the user's motivation. If the collected data indicates that the user will not reach his fitness goals based on his performance over multiple workouts, the lifestyle companion system can adjust the user's long-term goals to a level that may be more attainable for the user based on his past performance. Thus, a user's goals can be adapted either immediately or over time. In one embodiment of the present invention, a user's goals can be stored as goal data in the user's profile and the present invention can adapt the user's goals by adjusting the goal data.

In step 112, the lifestyle companion system also can dynamically adapt the user's activities based on the data collected in step 110. The lifestyle companion system can adjust a parameter of a current or future activity based on the collected data. For example, if the collected data indicates that the user will not reach a target performance metric (e.g., target number of calories burned or target heart rate) during a current fitness activity, the lifestyle companion system can increase the intensity or duration of the current fitness activity or a future fitness activity. If the collected data indicates that the user experienced activity levels over a predetermined period of time (e.g., during one day or over a number of days) that are lower than recommended or lower than that needed (e.g., to reach the user's weight loss goal), the lifestyle companion system can increase the level or intensity of future workout(s). If the collected data indicates that the user will not reach his fitness goals based on his performance over multiple workouts, the lifestyle companion system can increase the intensity or frequency of future workouts. Thus, a user's activities can be adapted either immediately or over time based on the collected data.

In step 114, the lifestyle companion system can provide the user with progress reports based on the goals expressed by the user in the user interview and the data collected about the user's activities. Progress reports can include information about the user's progress to date and trends in the user's progress. The information can be provided in charts and/or text. Progress reports also can include other information, e.g., personalized bio-rhythm charts (with automatic feeds from local weather), women's menstrual cycle, food types eaten, etc. Such functionality may allow a user to determine various patterns in the user's life.

Although FIG. 1 illustrates a flowchart having sequential steps, steps 100-114 do not have to be performed in the sequence shown. For example, as described above, the lifestyle companion system can suggest activities, references, and plug-in modules in step 104 based on data previously collected in accordance with step 110. Thus, one or more steps 100-114 can be reiterated. The lifestyle companion system also can perform one or more steps simultaneously. For example, the lifestyle companion system can simultaneously perform steps 108-112. In some embodiments of the present invention, some steps may be subsumed in other steps. For example, as described in greater detail below with respect to FIG. 7, the lifestyle companion system can provide a platform for a user to schedule activities during a user interview.

In some embodiments of the present invention, the lifestyle companion system can communicate with (e.g., obtain information from or provide information to) third party resources that can operate independently of the lifestyle companion system. For example, since many lifestyle planning and tracking activities revolve around timelines, the lifestyle companion system can be integrated with a calendar program similar to that offered under the trademark iCal™ by Apple Inc. Additional integrated programs also can include, for example, contacts lists, task lists, and/or group calendaring programs that permit participants, such as family members, to coordinate their respective schedules and exercise routines (e.g., MeetingMaker™ offered by PeopleCube of Waltham, Mass.). In one embodiment of the present invention, the task lists can include themed information, e.g., reading lists. The lifestyle companion system can obtain information from, for example, automatic feeds from local meteorological resources, food menus for restaurants, movie/theater schedules, TV schedules, etc. The progress reports provided in step 114 can be integrated into themed logs (e.g., food diary or pregnancy log), journals, and/or planning tools. In an alternative embodiment of the present invention, the lifestyle companion system can be configured to offer one or more of these resources itself (i.e., without communication with independent third party resources).

Figure 2:
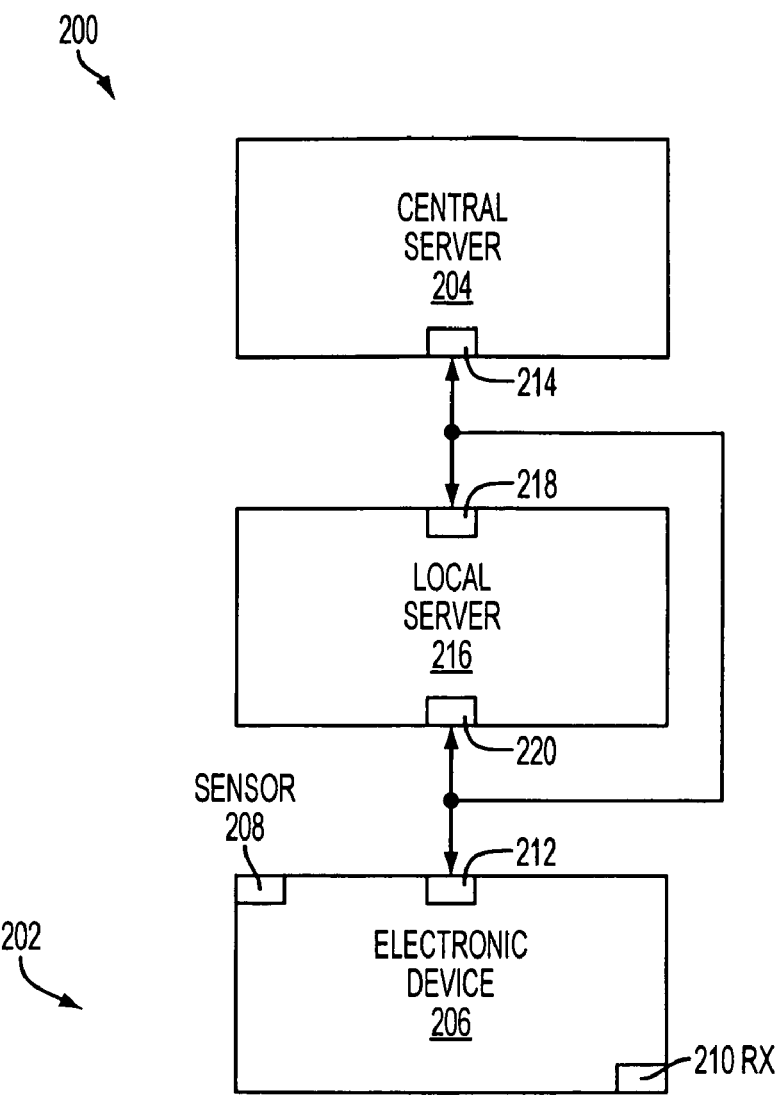
FIG. 2 illustrates hardware for the lifestyle companion system in accordance with one embodiment of the present invention.
Figure 2:
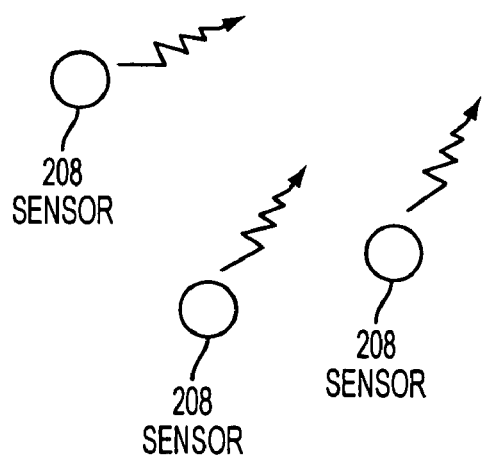

FIG. 2 illustrates hardware for the lifestyle companion system in accordance with one embodiment of the present invention. Lifestyle companion system 200 can include active tracking device 202 and central server 204. Tracking device 202 can incorporate electronic device 206 and one or more sensors 208. Electronic device 206 can include a controller, memory, first communication module 210 for receiving signals transmitted from sensors 208, and second communication module 212 for communicating with central server 204 and/or a local server. In an alternative embodiment of the present invention, first and second communication modules 210 and 212 can be combined as one component.

The controller of electronic device 206 can be configured to perform one or more of the steps described above with respect to FIG. 1. For example, the controller can be configured to accept sensor data from sensors 208 via communication module 210, direct the sensor data to be stored as part of the user's profile in the memory, determine how to adapt a user's goals based on the sensor data and goal data stored in the user's profile, and provide media cues to the user based on the sensor data and the adapted goals.

Sensors 208 can transmit data to first communication module 210 through a wire or by using a wireless communication protocol known in the art or otherwise. Sensors 208 can be attached to the user (e.g., in clothing or accessories). Alternatively, sensors 208 can be disposed within electronic device 206 or another device utilized by the user (e.g., fitness equipment described in greater detail below with respect to FIG. 22). If sensors 208 are disposed only within electronic device 206, the tracking device may not need first communication module 210. In one embodiment of the present invention, active tracking device 202 can include a portable media player similar to that sold under the trademark ipod™ by Apple Inc., and a sensor/receiver kit similar to the Nike+iPod Sport Kit sold by Apple Inc. and Nike, Inc. of Beaverton, Oreg.

In alternative embodiments of the present invention, data from sensors 208 can be transmitted directly or indirectly to central server 204 or local server 216. For example, sensors 208 can directly transmit its signals to central server 204 and/or local server 216, in addition to or instead of electronic device 206. Sensors 208 can indirectly transmit its signals to central server 204 and/or local server 216 using electronic device 206 as a conduit or through another conduit. If sensor data is transmitted indirectly through a conduit, the sensor data can undergo processing before it is transmitted to the central and/or local servers. As used herein, the term "sensor data" means any data directly generated by sensors 208 or any data derived from data directly generated by sensors 208.

In one embodiment of the present invention, central server 204 can include a controller, memory, and communication module 214. The controller of central server 204 can perform one or more of the steps described above with respect to FIG. 1. A user may download data collected about his activities from his active tracking devices 202 into central server 204. The memory of central server 204 can store the user's data in his user profile. Communication modules 212 and 214 can be configured to transmit signals between portable device 206 and central server 204 over a hard-wired or wireless network (e.g., the internet). Controllers of electronic device 206 and central server 204 can include one or more processors, ASICs, other types of circuits, or any combination thereof.

Lifestyle companion system 200 also can include local server 216, e.g., a user's personal computer. Local server 216 can serve as an intermediary between active tracking device 202 and central server 204. In some embodiments of the present invention, a user may interact with central server 204 through local server 216. A controller of local server 216 also can perform one or more of the steps described above with respect to FIG. 1. Thus, the process described above with respect to FIG. 1 can be executed by one or more of the controllers disposed in tracking device 202, central server 204, and local server 216. Local server 216 can communicate with active tracking device 202 and central server 204 using communication modules 218 and 220, which can be combined into one component.

User profiles can be stored in the respective memories of central server 204, local server 216, and/or tracking device 202. For example, user profile information can be stored in local server 216 for privacy reasons. User profile information also can be stored in central server 204 to facilitate access thereto by multiple user authorized entities or by the user from different geographic regions. For example, in one embodiment of the present invention, a user can authorize access of his user profile by the user's family member, employer, doctor, trained therapist or physical trainer, or other authorized entity. This can permit these user-authorized entities to review information associated with the user's profile (e.g., data collected about the user's activities) and/or suggest activities, references, and/or plug-in modules as described above with respect to step 104 of FIG. 1. User profile information also can be divided among device 202, central server 204, and/or local server 216.

In one embodiment of the present invention, central server 204 can provide a database from which the lifestyle companion system can select activities, references, and/or plug-in modules for suggestion to the user in step 104 of FIG. 1. Central server 204 also can permit the user to download activities, references, and/or modules from the same database and/or from a different database. Local server 216 can provide the platform for conducting the user interview and creating and scheduling user activities. This information, along with any media files providing audio and/or visual cues related to activities the user intends to perform, can be downloaded onto portable electronic device 206. Portable electronic device 206, in turn, can instruct the user in performing the activities. Advantageously, this can permit users to carry their most important information, lists, schedules, etc. with them. This also can permit a user to easily share such information with other authorized entities using, e.g., infra-red technology or via wireless or wired access to the internet or another type of network.

In alternative embodiments of the present invention, the central and local servers can be combined into one server. In another alternative embodiment of the present invention, the central server, the local server, and the portable electronic device can be combined into one device. For example, the portable electronic device can be configured to perform all the steps described with respect to FIG. 1.

In one embodiment of the present invention, electronic device 206 can include any portable, mobile, hand-held, or miniature consumer electronic device. Illustrative electronic devices can include, but are not limited to, music players, video players, still image players, game players, other media players (e.g., an iPod™ sold by Apple Inc.), music recorders, video recorders, cameras, other media recorders, radios, medical equipment, calculators, cellular phones, other wireless communication devices, personal digital assistances, programmable remote controls, pagers, laptop computers, printers, or combinations thereof.

Miniature electronic devices can have a form factor that is smaller than that of hand-held devices. Illustrative miniature electronic devices can include, but are not limited to, watches, rings, necklaces, belts, accessories for belts, headsets, accessories for shoes, virtual reality devices, other wearable electronics, accessories for sporting equipment, accessories for fitness equipment, key chains, or combinations thereof. Incorporation of miniature, wearable devices into existing items can be desirable because they require no additional effort by the user to use them.

FIGS. 3-23 show an illustrative application of the lifestyle companion system of FIGS. 1-2 to a fitness module in accordance with some embodiments of the present invention. While FIGS. 3-23 illustratively relate to a fitness module for the lifestyle companion system of the present invention, the systems and methods described herein can be applied to any other plug-in modules, including the nutrition module described in greater detail with respect to FIG. 25.

Figure 3:
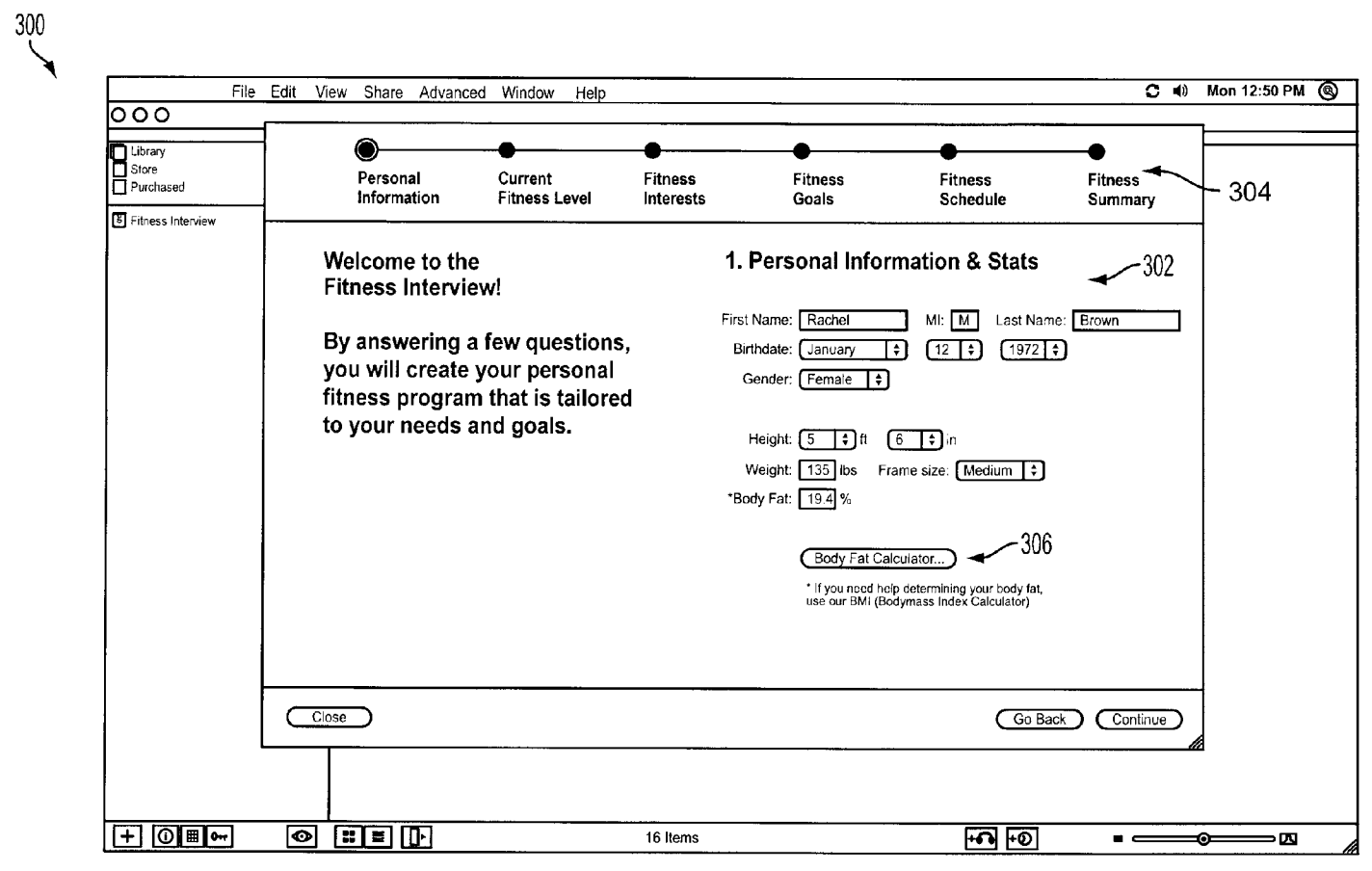

FIG. 3 shows an illustrative graphic user interface of a fitness welcome screen in accordance with one embodiment of the present invention. Screen 300 can include user input section 302 in which a user can input personal information and statistics as part of a user interview. For example, user input section 302 can include fields for the user's name, birth date, gender, and various bodily characteristics (e.g., weight, frame size, and a body fat metric). Other suitable fields also can be included on screen 300. Screen 300 also can include one or more links 306 to websites or other functionalities, e.g., a body fat calculator that allows a user to determine their individual body fat metric.

Screen 300 also can include interview progress indicator 304, which can indicate the user's progress through the user interview. Interview progress indicator 304 also can include selectable tabs that permit a user to navigate to other parts of the user interview. For example, in the embodiment shown in FIG. 3, the selectable tabs can permit a user to navigate to the parts of the fitness interview for user input of current fitness level, user input of fitness interests, user input of fitness goals, user input of a preferred fitness schedule, or display of a fitness summary.

Figure 4:
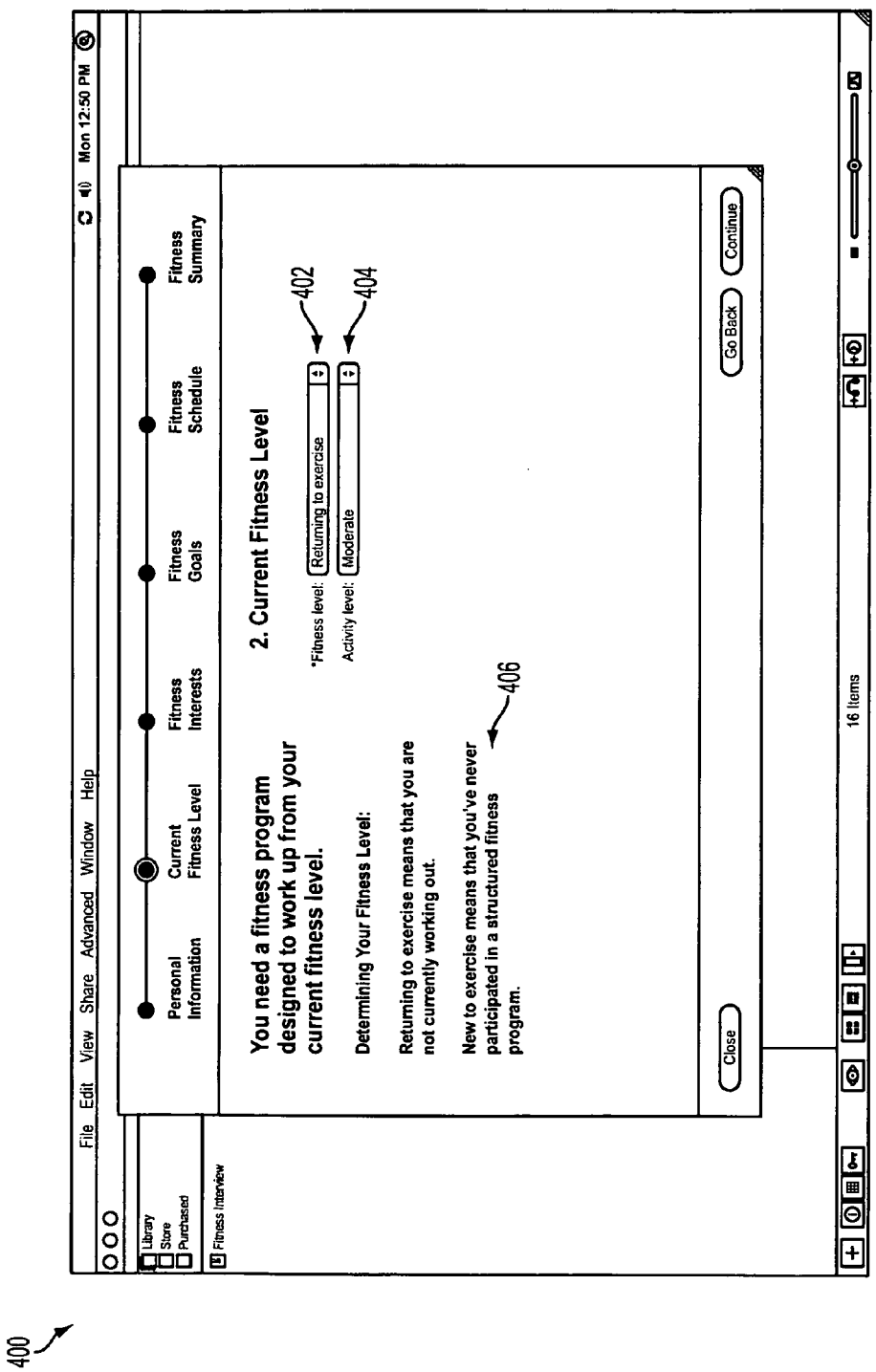
FIG. 4 shows an illustrative graphic user interface of a current fitness level screen in accordance with one embodiment of the present invention.

FIG. 4 shows an illustrative graphic user interface of a current fitness level screen in accordance with one embodiment of the present invention. Current fitness level screen 400 can include various fields for obtaining information about the user's current physical abilities. For example, fields can include a user's current fitness level 402, activity level 404, or any other suitable indicator. In one embodiment of the present invention, fields 402 and 404 can have selectable menus of predetermined options. This can permit the lifestyle companion system to define the predetermined options in instructional section 406 of screen 400.

Figure 5:
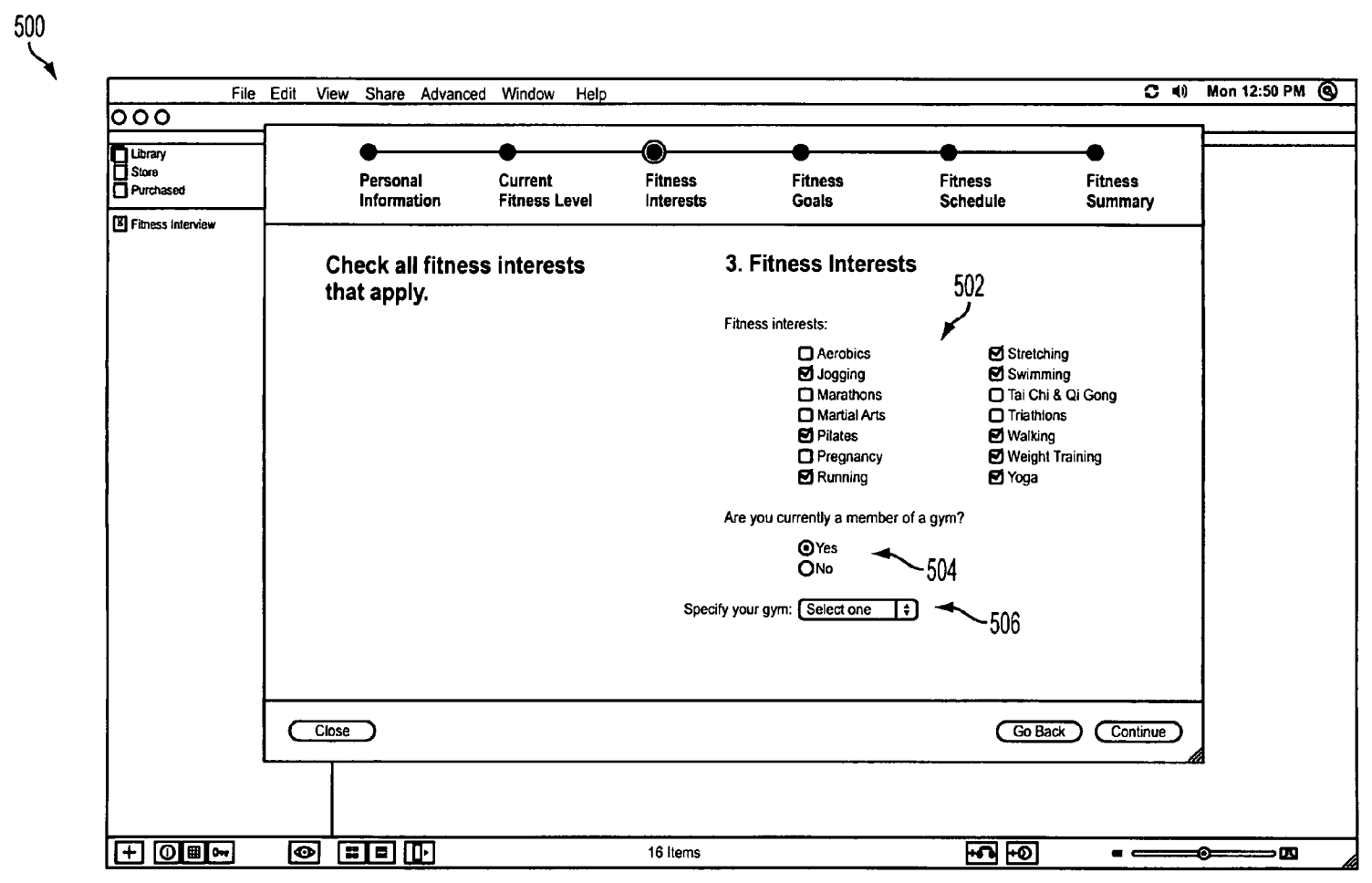

FIG. 5 shows an illustrative graphic user interface of a fitness interest screen in accordance with one embodiment of the present invention. Fitness interest screen 500 can include selectable menu of fitness interests 502, gym membership indicator field 504, and gym identifier field 506. Gym identifier field 506 can permit the user to identify the gym company and/or the specific branch of the gym that the user visits most frequently.

Figure 6:
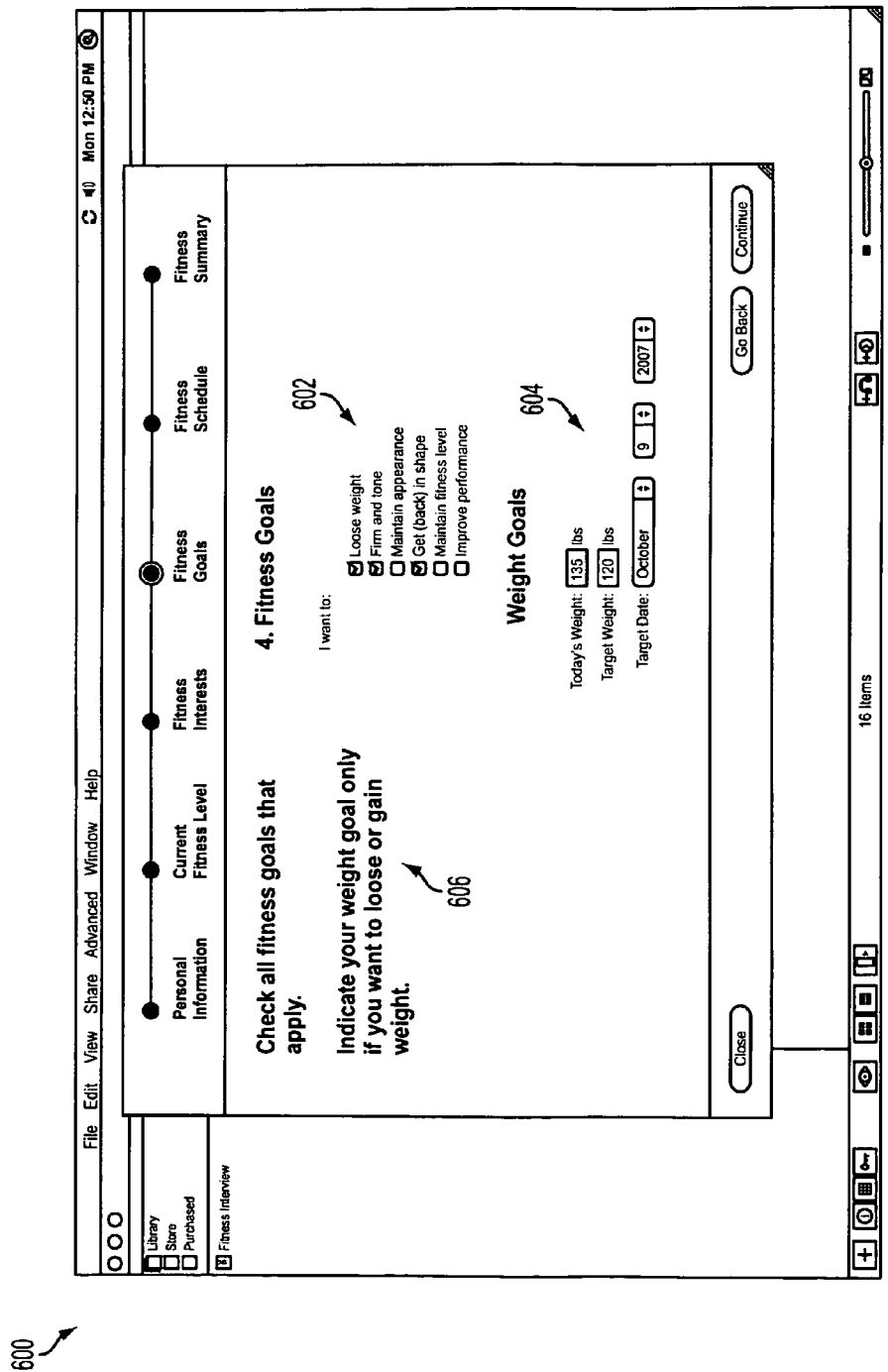
FIG. 6 shows an illustrative graphic user interface of a fitness goals screen in accordance with one embodiment of the present invention.

FIG. 6 shows an illustrative graphic user interface of a fitness goals screen in accordance with one embodiment of the present invention. Fitness goals screen 600 can include a selectable menu of fitness goals 602. Screen 600 also can have fields 604 in which a user can input specific values for one or more goals (e.g., the user's weight goals). In one embodiment, fields 604 can include fields for the user's current weight, target weight, and target date on which the user would like to achieve his target weight. Fitness goals screen 600 also can include instructional section 606, in which the lifestyle companion system can provide the user with graphic (e.g., text, still image and/or video) instructions and/or information related to the selectable menu 602 and fields 604.

Figure 7:
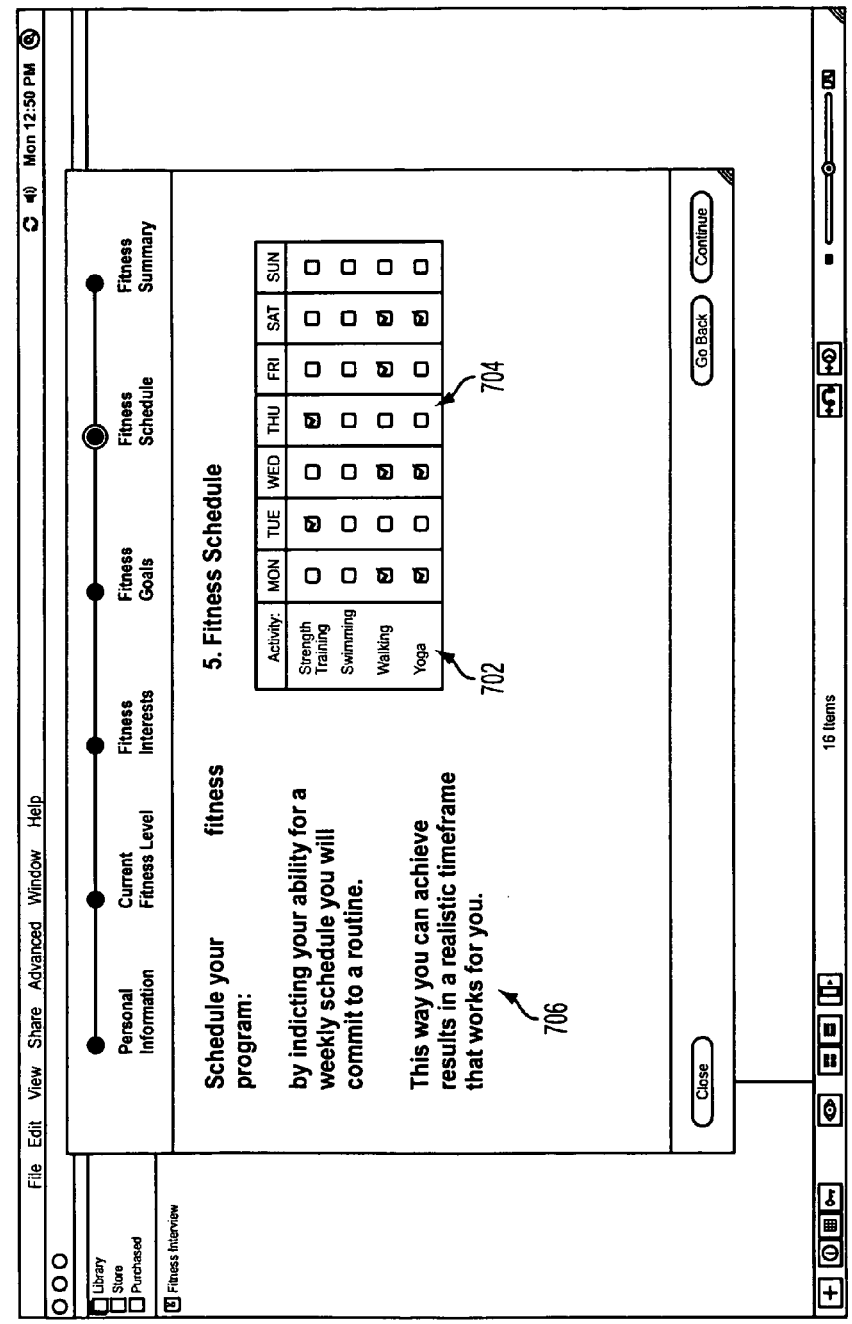
FIG. 7 shows an illustrative graphic user interface of a fitness schedule screen in accordance with one embodiment of the present invention.

FIG. 7 shows an illustrative graphic user interface of a fitness schedule screen in accordance with one embodiment of the present invention. Fitness schedule screen 700 can include menu of types of fitness activities 702 and selectable daily schedule 704. This can permit a user to identify the type of fitness activities the user prefers to undertake on each day of the week. This also can permit the user to identify the day(s) of the week in which the user is unavailable or unwilling to perform a fitness activity. Again, screen 700 can include instructional section 706 for providing the user with graphic instructions and/or information about the screen.

In one embodiment of the present invention, menu 702 can include fitness activity types suggested by the fitness module of the lifestyle companion system based on the user's interview responses to user fitness interests and goals (FIGS. 5-6). Alternatively, the categories can include a generic list that is not customized to the user.

Figure 8:
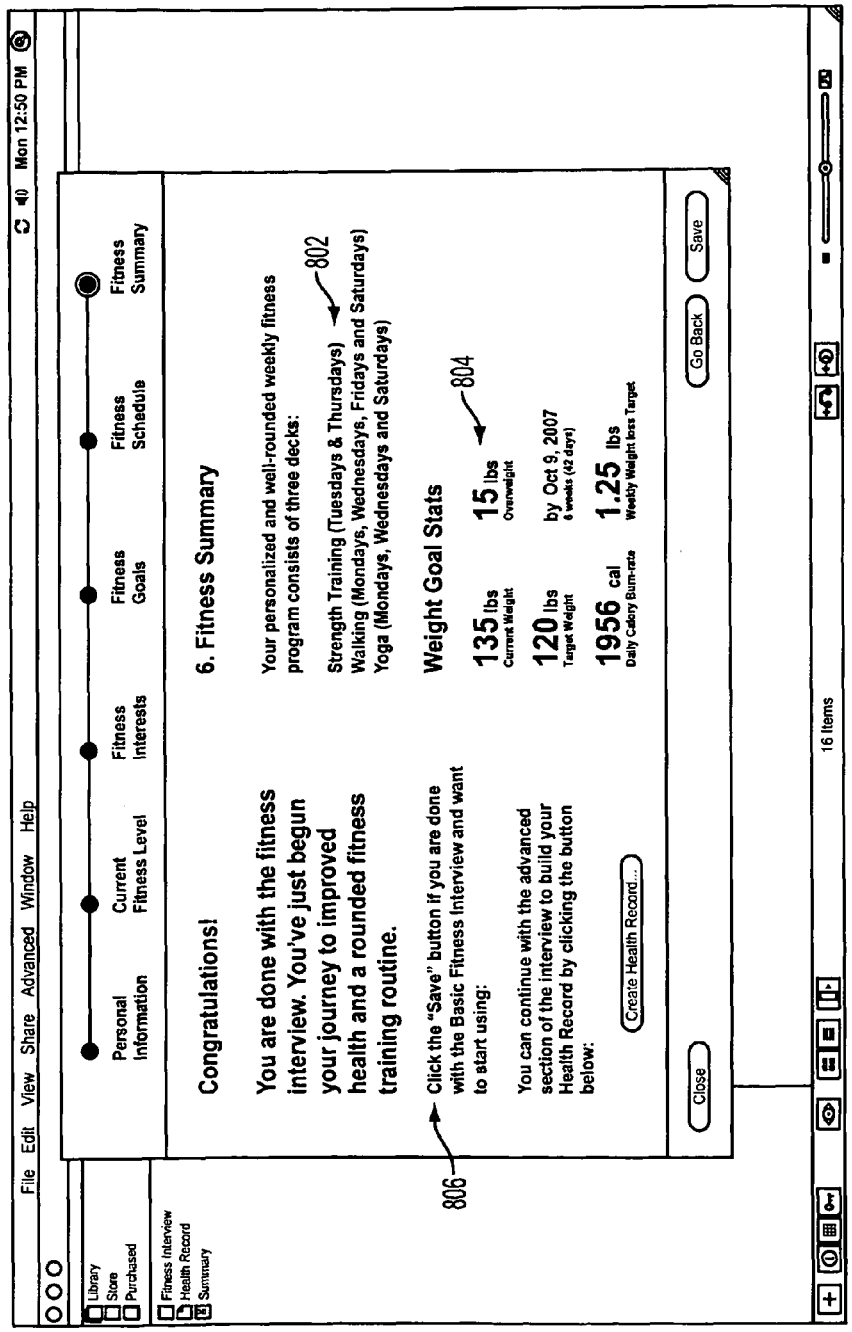
FIG. 8 shows an illustrative graphic user interface of a fitness summary screen in accordance with one embodiment of the present invention.

FIG. 8 shows an illustrative graphic user interface of a fitness summary screen in accordance with one embodiment of the present invention. For example, in section 802, fitness summary screen 800 can show a summary of the types of fitness activities and the corresponding days the user identified in fitness schedule screen 700 of FIG. 7. In section 804, fitness summary screen 800 also can show a summary of the user's weight statistics (e.g., the user's current weight, the amount by which the user is overweight, the user's target weight, and the date by which the user wishes to achieve the target weight). The lifestyle companion system also can calculate a user's target daily calorie burn-rate and weekly weight loss target based on the user's interview responses, and display that information in fitness summary screen 800 (e.g., in section 804). Again, screen 800 can include instructional section 806 for providing the user with instructions and/or information about the screen.

In one embodiment of the present invention, the lifestyle companion system can provide the user with the option to extend the user interview into additional interview functions, e.g., to compile the user's health record. Additional interview functions can be part of advanced functions of the fitness module or part of another plug-in module. For example, in the embodiment shown in FIG. 8, the interview function for compiling the user's health record can be part of the fitness module or part of a medical module that also is installed in the lifestyle companion system of the present invention. Thus, the lifestyle companion system of the present invention can seamlessly integrate multiple plug-in modules.

Figure 9:
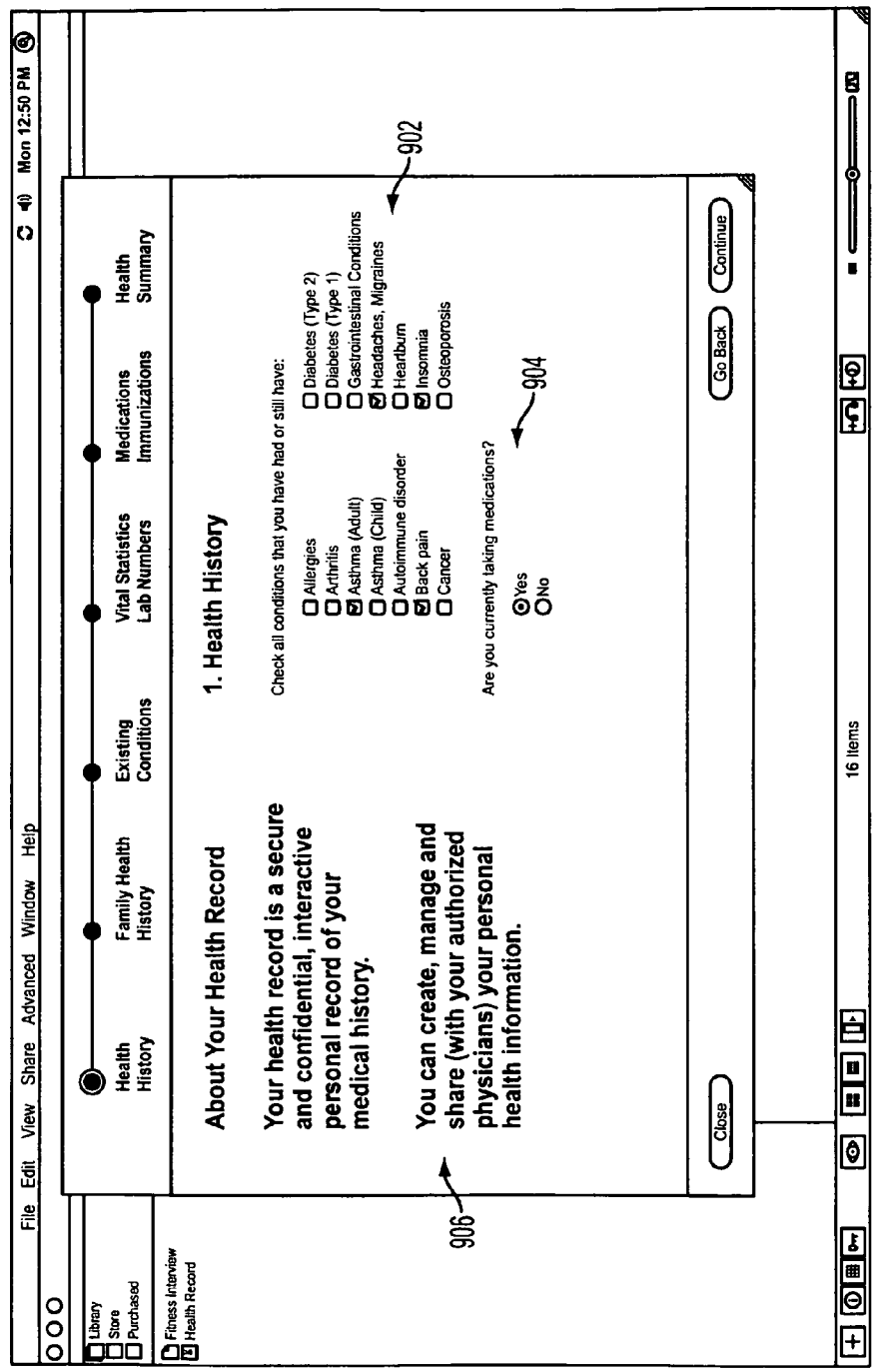
FIG. 9 shows an illustrative graphic user interface of a health history screen in accordance with one embodiment of the present invention.

FIG. 9 shows an illustrative graphic user interface of a health history screen in accordance with one embodiment of the present invention. Health history screen 900 can permit the user to identify medical concerns that, for example, can affect the user's ability to perform fitness activities. Health history screen 900 can include selectable menu 902 of health conditions that a user may have or have had. Health history screen 900 also can have medication indication field 904 through which the user can advise the lifestyle companion system of the present status of medication the user is taking. If the user indicates that he currently is taking medication, screen 900 can be updated to permit the user to input the name(s) of the medications the user is taking. The lifestyle companion system then can link to an internal or external database that can provide information about side effects of the medication or warnings. For example, some medications caution against increased sensitivity to sunlight. Thus, the lifestyle companion system may suggest activities that reduce sun exposure.

Figure 10:
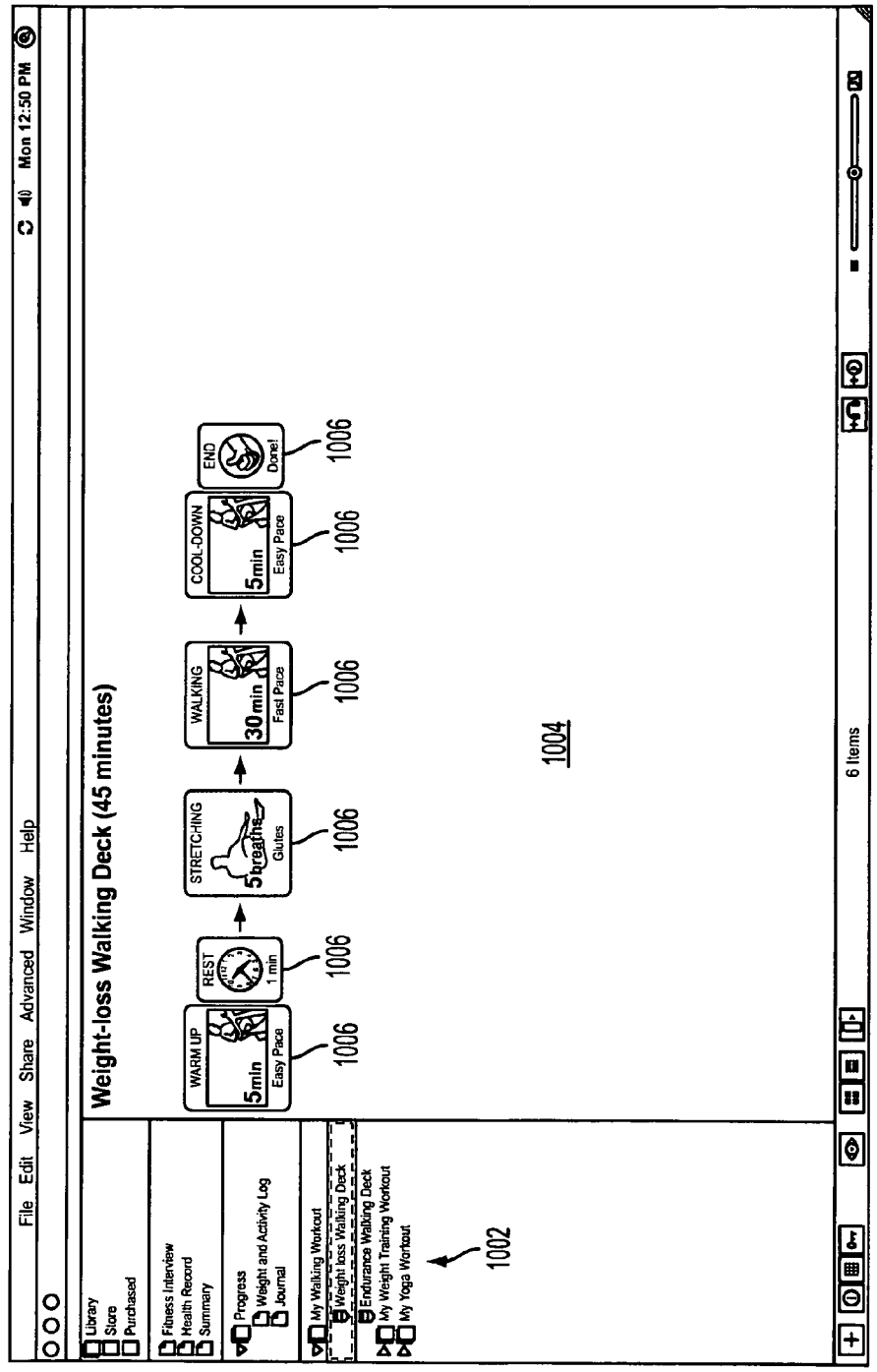
FIG. 10 shows an illustrative graphic user interface of a workout review screen in accordance with one embodiment of the present invention.

FIG. 10 shows an illustrative graphic user interface of a workout review screen in accordance with one embodiment of the present invention. Workout review screen 1000 can provide a platform through which the lifestyle companion system can permit a user to review a pre-compiled workout compilation that is suggested by the lifestyle companion system, composed by a third party and downloaded by the user, or previously composed by the user (e.g., as described in greater detail below with respect to FIG. 12). Each pre-compiled workout compilation can have one or more activities associated therewith. Thus, the lifestyle companion system of the present invention can select fitness activities for suggestion to the user by selecting a pre-compiled workout compilation.

In one embodiment of the present invention, the lifestyle companion system can provide a platform through which a user can purchase pre-compiled workout compilations from a central database of workout compilations (e.g., iTunes™). Those workout compilations can be choreographed workouts from third parties (e.g., for specific fitness facilities). Third parties can include, for example, fitness content partners (e.g., Gold's Gym) or user-authorized entities (e.g., the user's personal fitness trainer).

Workout review screen 1000 can include navigation section 1002 for navigating among the user's different workout compilations. Screen 1000 also can include compilation section 1004, in which building blocks 1006 of the workout compilation can be graphically shown. Each building block 1006 can represent an individual fitness activity or a rest time activity. As described in greater detail below with respect to FIG. 12, each building block 1006 can be associated with adjustable fitness parameters (or settings) preset by the lifestyle companion system (e.g., based on the user's interview responses or based on default values) and adjusted by the user, e.g., in a manner described in greater detail below with respect to FIG. 12. The associated fitness parameters (or settings) can include duration, intensity, equipment needed, repetitions, sets, any other suitable parameter (or setting) related to a fitness activity, or any combination thereof. Each building block 1006 can provide one or more graphic representation of the associated fitness activity and/or the associated fitness parameters (or settings).

In one embodiment of the present invention, the workout compilation illustrated in FIG. 10 can be one that is suggested by the lifestyle companion system based on a user's interview responses (e.g., an interest in weight loss, an interest in walking, and no access to fitness facilities or equipment). The lifestyle companion system can select the entire workout compilation from a database of pre-compiled workout compilations based on the user's interview responses. Alternatively, the lifestyle companion system can select the workout compilation from the database and customize the adjustable fitness parameters (or settings) of each building block based on the user's interview responses.

Alternatively, the lifestyle companion system can compose the workout compilation entirely based on the user's interview responses. For example, the lifestyle companion system can select each building block, arrange the order in which the user will be instructed to perform the fitness activities associated with the building blocks, and customize the fitness parameters (or settings) associated with each building block based on the user's interview responses. In one embodiment of the present invention, the lifestyle companion system can select one or more of the building blocks pseudo-randomly from a subset of a database of activities (e.g., a subset that includes activities that themselves are selected from the database based on the user's profile).

Figure 11:
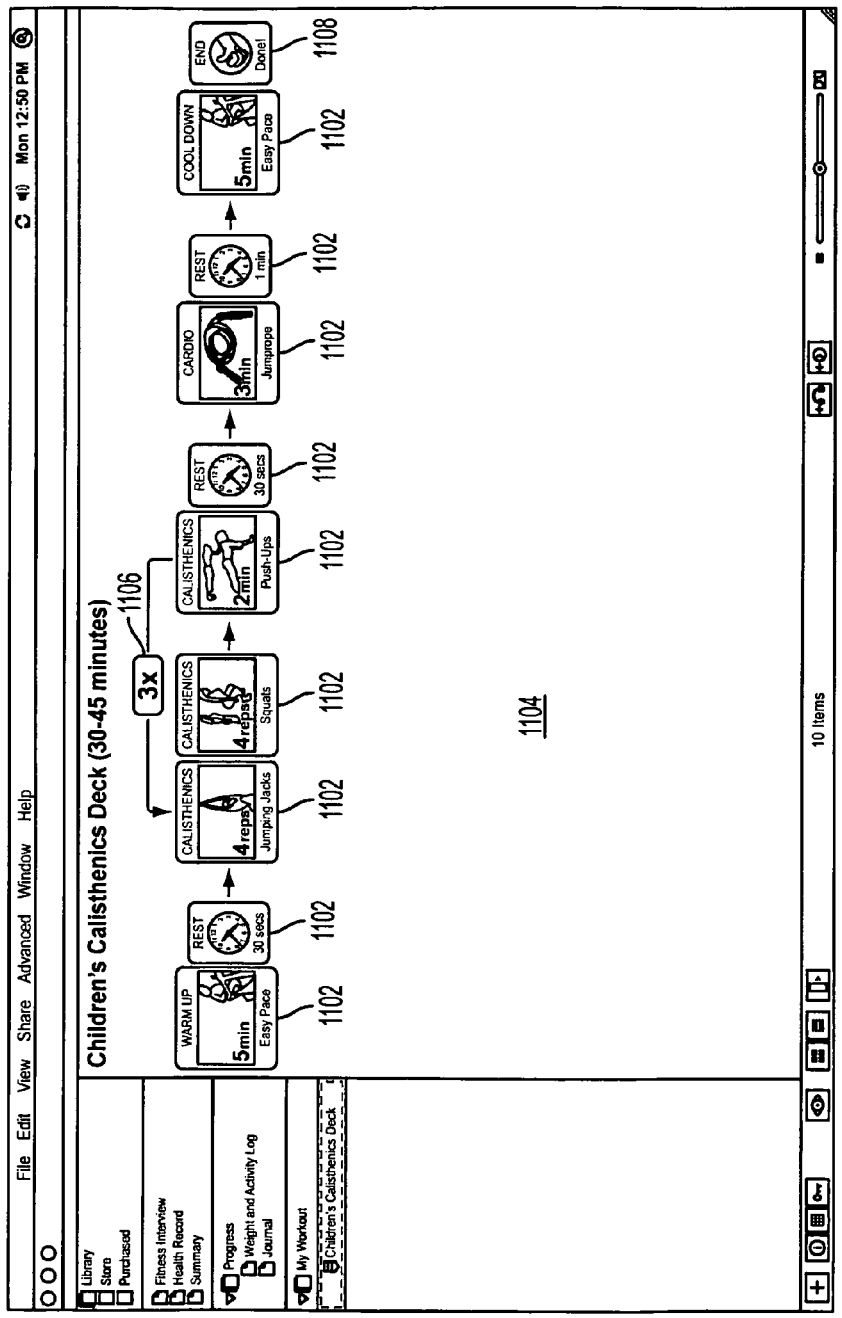
FIG. 11 shows an illustrative graphic user interface of an alternative workout review screen with a repetition feature in accordance with one embodiment of the present invention.

FIG. 11 shows an illustrative graphic user interface of an alternative workout review screen in accordance with one embodiment of the present invention. Like workout review screen 1000, workout review screen 1100 also can include compilation section 1104 in which building blocks 1102 can be provided. Workout review screen 1100 also can include repetition indicator 1106 and completion indicator 1108. Repetition indicator 1106 can graphically indicate the number of times the workout compilation is encoded to instruct the user to repeat a set of fitness activities. The fitness activities to be repeated can include those represented by the building blocks spanned by the repetition indicator. In the embodiment of FIG. 11, the repeated fitness activities include jumping jacks, squats, and push-ups.

Figure 12:
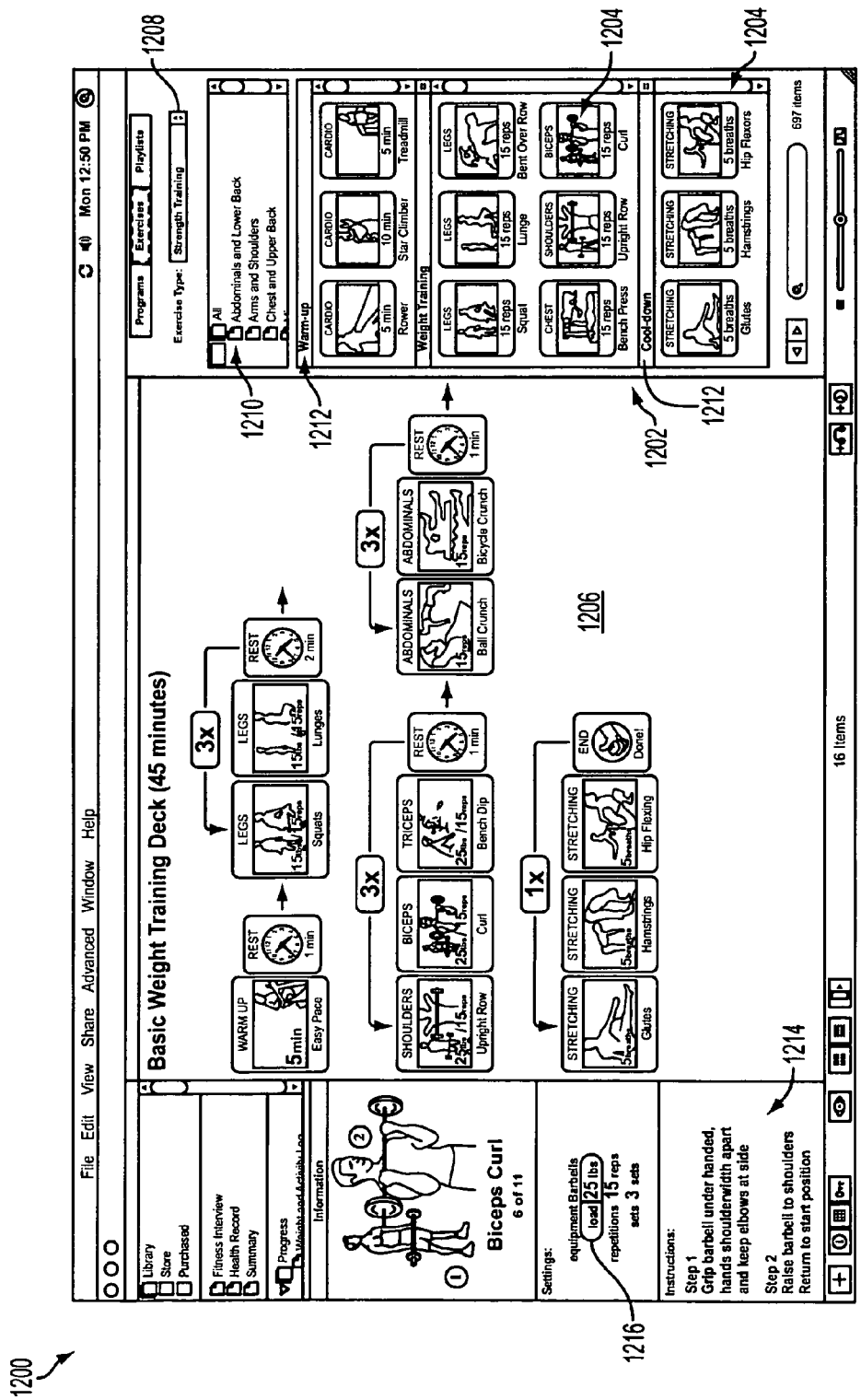
FIG. 12 shows an illustrative graphic user interface of a user workout composition screen in accordance with one embodiment of the present invention.

FIG. 12 shows an illustrative graphic user interface of a user workout composition screen in accordance with one embodiment of the present invention. Composition screen 1200 can provide a platform through which the lifestyle companion system can permit a user to (1) compose his own workout compilation, (2) customize suggested workout compilations and fitness activities, and/or (3) customize workout compilations and fitness activities composed by a third party.

Composition screen 1200 can include selectable menu 1202 of building blocks 1204. When composing a workout compilation, a user or other authorized entity can select building blocks 1204 of fitness activities from menu 1202 and arrange the selected building blocks in compilation section 1206 in the order in which the workout compilation should instruct the user to perform the selected fitness activities. In menu 1202, fitness building blocks 1204 can be sorted according to the exercise type indicated by user-selectable field 1208, body area or muscle group indicated by user selectable field 1210, and the phase of the workout compilation (e.g., warm-up, cool-down, etc.) indicated by fields 1212.

The fitness building blocks included in menu 1202 can include a default group of building blocks, selections culled from a database of building blocks based on the user's interview responses, or building blocks suggested by a third party that may or may not be authorized by the user. For example, the building blocks included in menu 1202 can be suggested based on the user's fitness interests, preferred types of fitness activities, availability of equipment at the gyms frequented by the user, etc.

Each building block can be associated with one or more adjustable fitness parameters. By adjusting the fitness parameter(s) associated with a fitness activity, the fitness activity can be customized to the abilities and goals of a user. The fitness parameters (or settings) associated with each building block can have default values, values suggested by the lifestyle companion system based on the user's profile (e.g., the user's fitness or weight loss goals, the user's access to fitness facilities and equipment), or values suggested by a third party that may or may not be authorized by the user.

The fitness parameters also can be set based on user-specified values. To permit a user to set one or more fitness parameters associated with a fitness activity, screen 1200 also can incorporate instructional section 1214, in which instructional fitness parameters 1216 are provided. The lifestyle companion system can permit a user or other user authorized entity to set one or more of the displayed instructional fitness parameters by adjusting the value of the parameter shown in instructional section 1214. Instructional section 1214 also can provide graphic instructions on how to perform the fitness activity associated with the selected building block. For example, instructional section 1214 can provide textual instructions, still images, and/or an instructional video.

Figure 13:
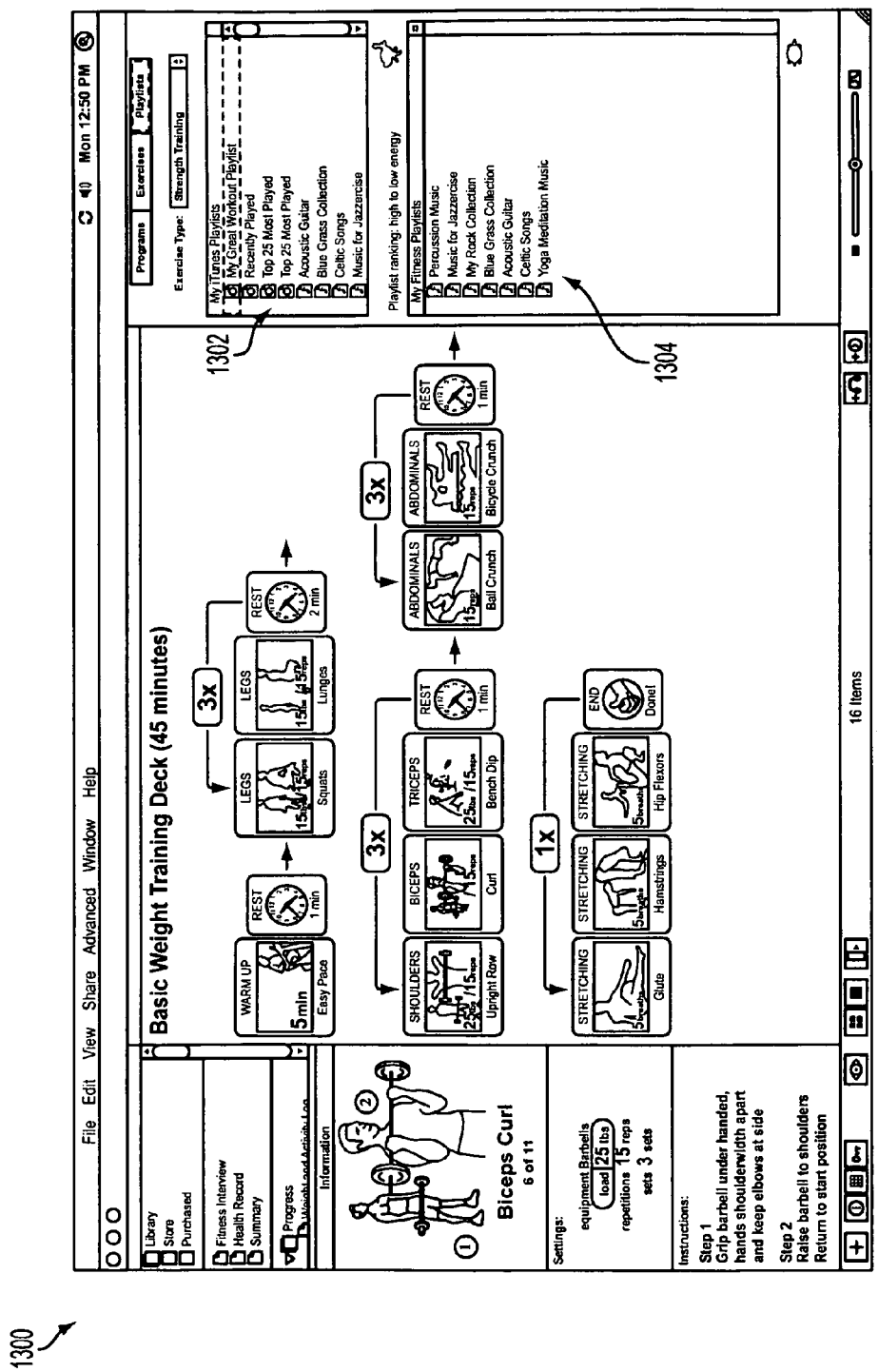
FIG. 13 shows an illustrative graphic user interface of a user workout composition screen having a media playlist menu in accordance with one embodiment of the present invention.

FIG. 13 shows an illustrative graphic user interface of a user workout composition screen having a media entertainment playlist menu in accordance with one embodiment of the present invention. Composition screen 1300 can provide a platform through which the lifestyle companion system can permit a user to associate entertainment media playlists with individual fitness activities and/or the entire workout compilation. Media entertainment playlists can include playlists of audio and/or visual (e.g., still image or video) entertainment files. Thus, when the user is exercising in accordance with the fitness activities associated with a workout compilation, the user can be entertained and motivated.

An entertainment playlist can include one or more media files. As used herein, an entertainment playlist refers to one or more media files containing information that is unrelated to an activity that the user will be directed to perform during playback of the entertainment playlist. For example, an entertainment playlist can include one or more music files, podcasts, music video files, TV show files, movie files, etc. In contrast, media files that instruct the user on performance of an activity associated with a workout compilation are considered instructional files.

Composition screen 1300 can include entertainment playlist menu 1302. Entertainment playlist menu 1302 can include, for example, a user's iTunes™ playlist menu, a video menu, a photo menu, a song menu, a podcast menu, a radio station broadcast menu, or any combination thereof. The user can select one or more entertainment playlists from entertainment playlist menu 1302 and assign an energy rank to each of the selected entertainment playlists according to energy level of the corresponding media tracks. The ranked entertainment playlists can be displayed in section 1304 of screen 1300. The entertainment playlists can be manually assigned energy ranks by the user or automatically assigned energy ranks by the lifestyle companion system in accordance with, for example, the tempo of songs in each entertainment playlist.

In one embodiment of the present invention, the lifestyle companion system can suggest associations of entertainment playlists with fitness activities. For example, the lifestyle companion system can select one or more playlists to associate with one or more fitness activities based on the expected intensity of the activities and the energy ranks of the entertainment playlists.

During performance of an activity, one or more of the entertainment playlists can be played. The present invention can playback entertainment playlists that have been pre-associated with a workout or fitness activity, permit the user to manually control the specific entertainment playlist played during an activity, or allow the lifestyle companion system to automatically select entertainment playlists based, for example, on the energy rank of the entertainment playlist and the intensity of the activity.

In one embodiment of the present invention, the lifestyle companion system also can permit a user to assign one or more media files as "power songs." Power songs may be predetermined audio files that a user can preferably and instantly queue up at the push of a button for extra motivation.

In one embodiment of the present invention, the lifestyle companion system can permit a user to manually associate one or more playlists with one or more building blocks. Alternatively, the lifestyle companion system can automatically associate one or more playlists with one or more building blocks according to the relative expected energy level required by the fitness activities associated with the building blocks. For example, the lifestyle companion system can automatically associate lower energy playlists with fitness activities to be performed during the beginning or end of a workout (e.g., warm-up or cool-down). Similarly, higher energy playlists automatically can be associated with fitness activities to be performed during the middle of the workout. Thus, when the user is exercising in accordance with the workout compilation, the lifestyle companion system can play media having energy levels that are appropriate for the types of fitness activities being performed by the user.

In operation, a user can begin composing a workout composition by dragging one or more selected building blocks to composition section 1206 and arrange them in the order desired. Alternatively, the user can retrieve a pre-compiled workout compilation from memory or download a pre-compiled workout compilation from a database. If the user so desires, the user then can set or adjust the value of one or more fitness parameters 1216 of one or more fitness activities. Thereafter, the user can associate entertainment media playlists to the workout compilation or permit the lifestyle companion system to associate entertainment media playlists to the workout compilation based on the energy rank of the playlist and the expected energy levels of individual fitness activities and/or all of the activities associated with the workout compilation. Thereafter, the lifestyle companion system can compile the workout compilation, creating an activity file. The activity file can associate all of the media files, fitness parameters, and other information related to the workout compilation composed by the user.

Once a user has completed the user interview and has reviewed and/or composed one or more workout compilations, the user can begin exercising in accordance with one or more of the workout compilations. In one embodiment of the present invention, the user can compose workout compilations on a local server (e.g., the user's PC) and download the workout compilations onto a portable electronic device that the user can carry with him while exercising. The portable electronic device can provide both audio and visual cues to the user that relate to the workout compilation and to any entertainment playlists being played back during the workout.

Once the user has composed one or more workout compilations, the user also can share the workout compilation with user-authorized entities, e.g., with the user's doctor, trainer, physical therapist, friend, or any other entity authorized by the user.

FIGS. 14-21 show illustrative graphic user interfaces during playback of a workout compilation on an electronic device in accordance with one embodiment of the present invention. Electronic device 1400 can include touchscreen display 1402 on which the electronic device can display visual cues and user input components 1404-1412 to permit user interaction with the electronic device and/or the workout compilation. Touchscreen display 1402 can sense when a user's finger(s) and/or hands approaches, touches, or slides across the screen. User input components 1404-1412 can be hard-wired user input components or virtual user input components that are part of touchscreen display 1402. For example, user input components 1404-1412 can include one or more buttons, a touchpad, a touchscreen display, electronics for accepting voice commands, antennas, infrared ports, or combinations thereof. User input components 1404-1412 also can include a hard-wired and/or virtual clickwheel similar to that incorporated into some models of the iPod™. The clickwheel can have hardwired or virtual buttons and a track around which a user can run his finger to initiate scrolling.

Figure 14:
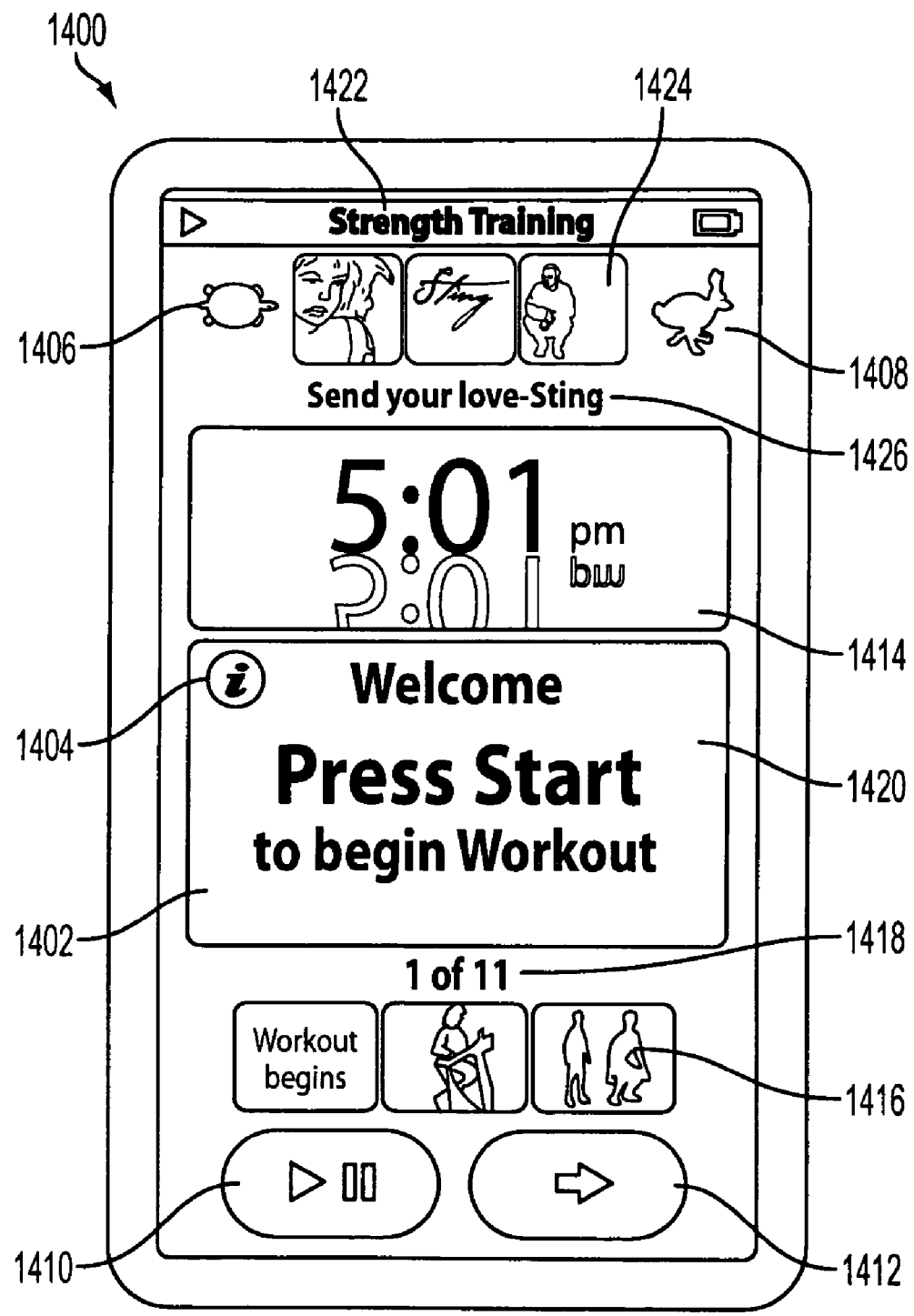
FIGS. 14-21 show illustrative graphic user interfaces during playback of a workout compilation on a portable electronic device in accordance with one embodiment of the present invention.

FIG. 14 shows an illustrative graphic user interface of a welcome screen on electronic device 1400 in accordance with one embodiment of the present invention. Interface 1414 can provide visual cues related to a workout compilation being played back by the electronic device. For example, visual cues can include fitness activity filmstrip 1416, progress indicator 1418, instructional section 1420, and exercise type indicator 1422.

Fitness activity filmstrip 1416 can include graphic representations of previous, current, and future fitness activities that the workout compilation has, is, and will direct the user to perform. As the user advances through the workout compilation, electronic device 1400 will update fitness activity filmstrip 1416 accordingly based on data received by sensors 208 and/or manual user input informative of advancement from a current activity to a future activity. For example, when the sensor data indicates that the user has completed the current activity (e.g., performed the current activity in accordance with the associated fitness parameters), electronic device 1400 can update the filmstrip by updating the graphics (e.g., by adding a graphic representing the next future activity and removing the graphic of the last previous activity).

Progress indicator 1418 can indicate the progress of the user in performing the fitness activities of the currently loaded workout compilation. In one embodiment of the present invention, progress indicator 1418 can indicate the total number of fitness activities associated with the currently loaded workout compilation and the location of the current fitness activity within the total number. In one embodiment, electronic device 1400 can automatically update progress indicator 1418 based on data collected from sensor(s) 208 of FIG. 2 about the user's performance. For example, once data collected from sensors 208 indicates that the user has completed a fitness activity of the current workout compilation in accordance with the associated fitness parameters, electronic device 1400 can automatically update progress indicator 1418 accordingly, in addition to displaying visual cues for the next fitness activity associated with the current workout compilation. The electronic device also can update progress indicator 1418 based on user input signals that indicate the user's desire to advance onto the next activity.

In the welcome screen of FIG. 14, instructional section 1420 can provide visual instructions for initiating the workout and information about the workout itself (e.g., total duration, name of the workout, etc.). Instructional section 1420 also can include virtual user input component 1404, which the user can actuate to obtain more detailed information about the currently loaded workout compilation. In one embodiment of the present invention, detailed information accessible via virtual user input component 1404 can include an index of the fitness activities associated with the currently loaded workout compilation, an example of which is described in greater detail below with respect to FIG. 21.

Exercise type indicator 1422 can indicate the type of exercise(s) for which the currently loaded workout compilation is targeting (e.g., strength training). Other types of exercise types can include, for example, weight loss, yoga, calisthenics, etc.

Interface 1414 also can provide visual representations of entertainment playlist(s) associated with the workout compilation, e.g., as described in greater detail above with respect to FIG. 13. For example, interface 1414 can provide entertainment filmstrip 1424 having graphics indicative of the entertainment tracks associated with the entertainment playlist currently being played. Interface 1414 also can provide graphics 1426 identifying the title and artist of the entertainment track currently being played. Interface 1414 also can provide virtual user input components 1406 and 1408, which the user can actuate to change the entertainment playlist currently being played. For example, the user can actuate virtual user input component 1406 when the user desires to play an entertainment playlist having an energy rank that corresponds to a lower energy level. The user can actuate virtual user input component 1408 when the user desires to play an entertainment playlist ranked having an energy rank that corresponds to a higher energy level (e.g., when the user wants to be motivated by songs having a faster tempo). Alternatively, electronic device 1400 can automatically link entertainment playlists to fitness activities and/or workout compilations based respectively on the energy ranks of the entertainment playlists and the expected intensity of the fitness activities and workout compilations. As described with respect to FIG. 13, the energy levels of the entertainment playlists can be manually ranked by the user or automatically rated by the lifestyle companion system.

Figure 15:
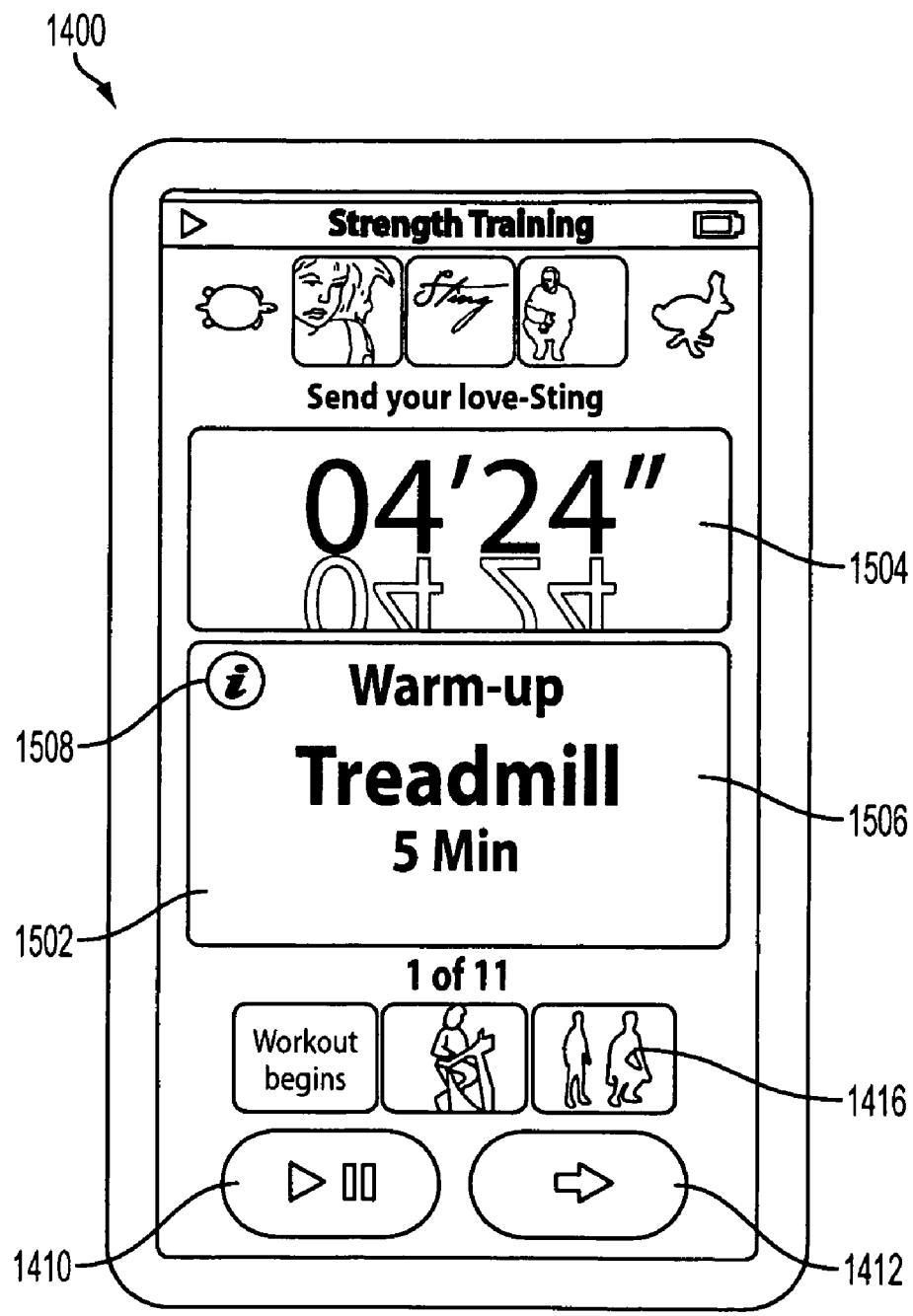

FIG. 15 shows an illustrative graphic user interface provided by electronic device 1400 during one fitness activity in accordance with one embodiment of the present invention. In addition to one or more of the visual cues provided by interface 1414 of FIG. 14, interface 1502 also can provide additional visual cues related to the workout compilation being played back by the electronic device. Such additional visual cues can include timer 1504 and textual information 1506 regarding the fitness activity the workout compilation is instructing the user to perform. Timer 1504 can be a countdown timer that indicates the amount of time remaining in the current fitness activity or the amount of time elapsed since the beginning of the current fitness activity. Textual information 1506 can provide information about the fitness activity the workout compilation is directing the user to perform, e.g., the phase of the workout compilation (e.g., warm-up, cool-down, etc.), the title of the fitness activity, the amount of time in which the user should perform the indicated fitness activity, etc. In one embodiment of the present invention, electronic device 1400 also can provide audio cues about information similar or identical to that provided as textual information 1506.

Electronic device 1400 also can provide hard-wired or virtual user input components 1410, 1412, 1508 for the user to interact with the workout compilation currently being played. For example, a user can actuate user input component 1508 to obtain more detailed information about the current fitness activity. In one embodiment of the present invention, detailed information accessible via virtual user input component 1508 can include instructions for performing the current fitness activity and/or more detailed information about the fitness parameters associated with the current fitness activity (e.g., as described in greater detail below with respect to FIGS. 17 and 18).

A user can actuate user input component 1410 to play, pause, and/or stop playback of the current workout compilation. For example, a single short press of the user input component can instruct the electronic device to pause playback of the workout compilation, while a two short presses of the user input component can instruct the electronic device to stop the playback of the workout compilation.

A user also can actuate virtual user input component 1412 to advance onto the next successive fitness activity in the workout compilation. In an alternative embodiment of the present invention, electronic device 1400 also can be configured to permit the user to navigate to a different fitness activity associated with the current workout compilation by actuating one of the graphic representations of fitness activity filmstrip 1416. For example, to advance onto the next fitness activity or return to a previous fitness activity, the user can actuate the graphic representation of that fitness activity on filmstrip 1416, e.g., by pressing on the appropriate representation. As described in greater detail below with respect to FIG. 19, electronic device 1400 also can advance onto the next successive fitness activity automatically when the collected sensor data indicates that the user has completed the current activity. When electronic device 1400 advances onto the next successive fitness activity, the electronic device can update the activity information displayed on its display to reflect information (e.g., instructions) for that next activity.

Figure 16:
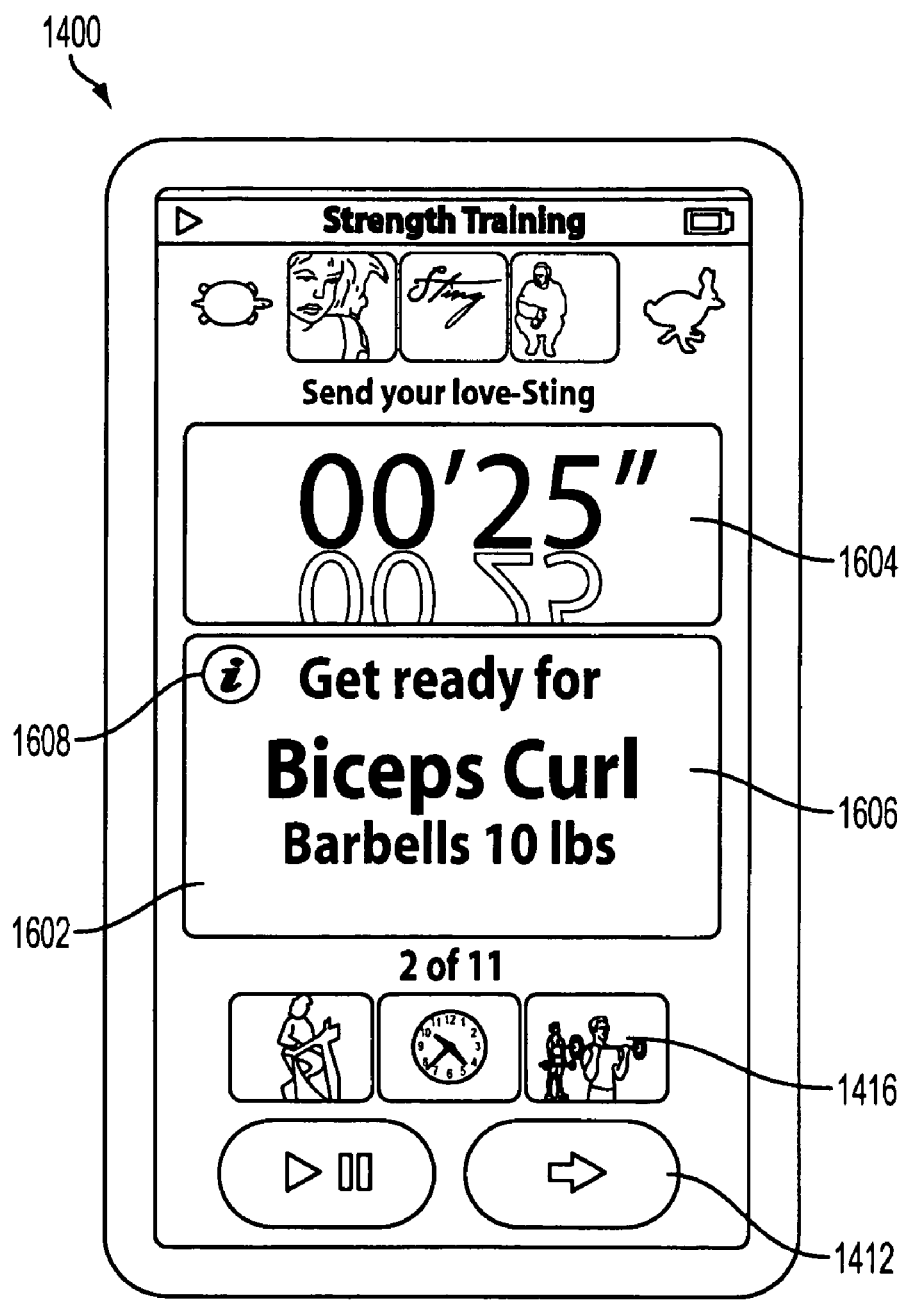

FIG. 16 shows an illustrative graphic user interface provided by electronic device 1400 during a rest time activity in accordance with one embodiment of the present invention. Like interface 1502 of FIG. 15, interface 1602 also can have timer 1604. To indicate that the present activity is a rest time activity, fitness activity filmstrip 1416 can depict a graphical representation of time (e.g., a clock). If a user is ready to begin the next fitness activity before the time allocated for the rest time activity has timed out, the user may manually advance the workout compilation to the next fitness activity by actuating the representation of the desired fitness activity on filmstrip 1416 or actuating user input component 1412.

Interface 1602 also can incorporate instructional section 1606 to provide visual instructions for the next fitness activity. For example, in the embodiment shown in FIG. 16, instructional section 1606 can instruct the user to prepare for the next fitness activity (e.g., biceps curl) by gathering the proper equipment for the activity (e.g., 10 lbs. barbells). Instructional section 1606 also can include user input component 1608, which, when actuated, can reveal more detailed information about the next fitness activity, e.g., as described in greater detail below with respect to FIGS. 17 and 18.

Figure 17:
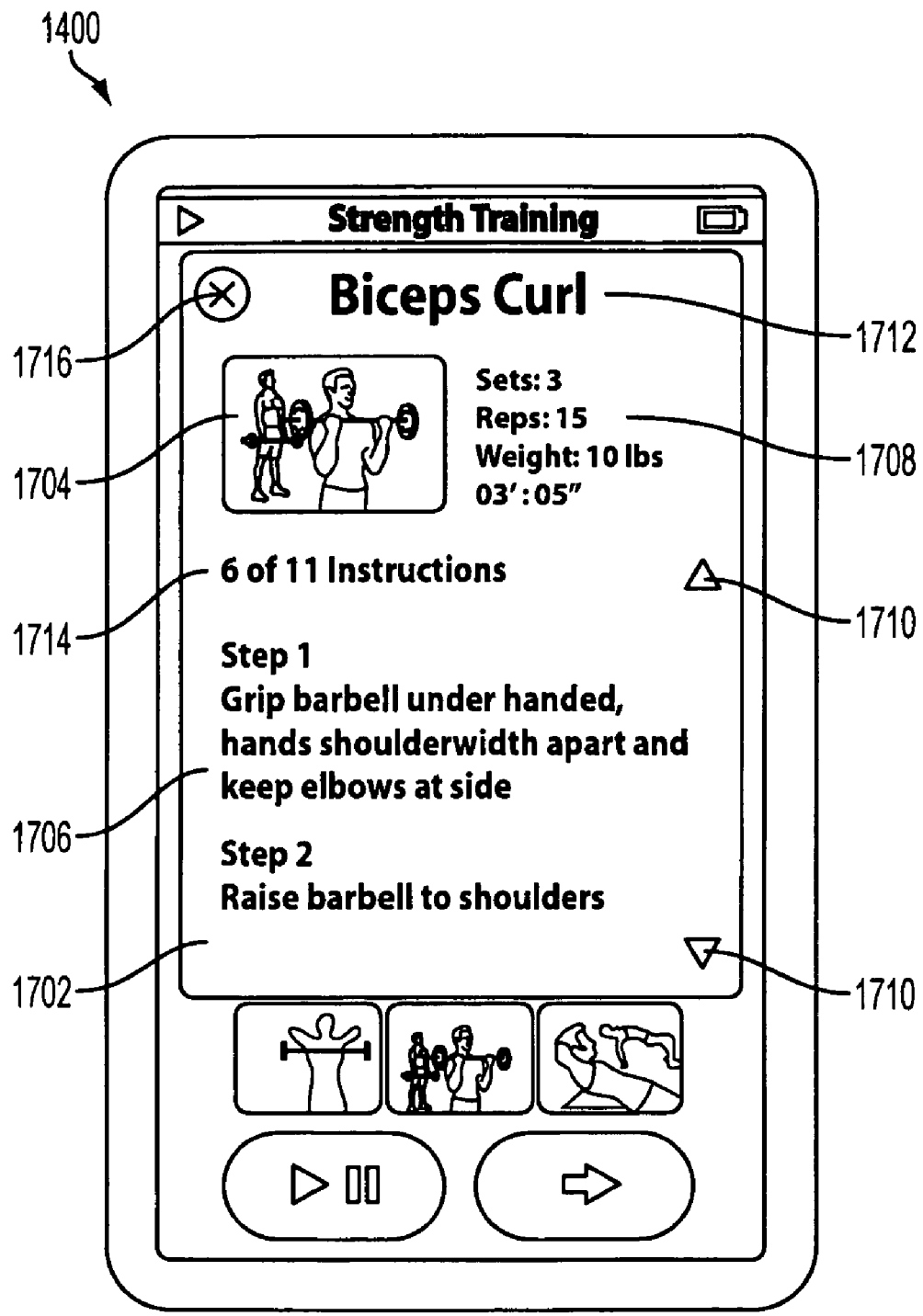

FIG. 17 shows an illustrative graphic user interface provided by electronic device 1400 in accordance with one embodiment of the present invention. Interface 1702 can provide a platform through which the lifestyle companion system can provide the user with more detailed information about a fitness activity. For example, interface 1702 can provide a platform through which the lifestyle companion system can provide the user with pictorial instructions 1704 for the fitness activity, detailed textual instructions 1706 for the fitness activity, and instructional fitness parameters 1708 associated with the fitness activity.

Pictorial instructions 1704 and textual instructions 1706 can provide instructions related to the proper way to perform the fitness activity currently being displayed on interface 1702. For example, the instructions can relate to proper posture during the routine, proper breathing techniques, and/or other information related to the proper way to perform the fitness activity. If the textual instructions require more space than available on interface 1702, electronic device 1400 can permit the user to scroll through the textual instructions by using user-actuable scroll bar 1710 on interface 1702 or another user interface component (e.g., a hard-wired scroll wheel). Pictorial instructional 1704 can include one or more still images and/or videos.

As discussed above with respect to FIG. 12, adjustable fitness parameters 1708 can be considered as instructions that guide the user in performing a fitness activity. Fitness parameters 1708 can include, e.g., the number of sets the workout compilation is instructing the user to perform, the number of repetitions per set the workout compilation is instructing the user to perform, the equipment the workout compilation is instructing the user to use in performing the fitness activity, the amount of time the workout compilation is instructing the user to allocate in performing the fitness activity, the entertainment playlist or file the user programmed the workout module to play during the fitness activity, etc. Fitness parameters 1708 can reflect default values, values suggested by the lifestyle companion system based on the user's profile or previously collected sensor data, values programmed by a third party and downloaded by the user in step 105 of FIG. 1, or values programmed by the user in step 105 using, for example, interface 1200 of FIG. 12. Thus, the fitness parameters can have default values or values customized for the user.

In one embodiment of the present invention, electronic device 1400 can permit the user to adjust one or more user-programmable parameters of a fitness activity in real-time during playback of the workout compilation. The user can select and adjust the parameters by using a virtual or hard-wired user input component. The electronic device can facilitate the selection by visually distinguishing the selected parameter. Once the user has adjusted one or more parameters, the electronic device can proceed to continue playing back the currently loaded workout compilation in accordance with the adjustments to the fitness parameters. For example, if the user changes the number of sets from 3 sets to 2 sets, the adjustment can be reflected in the fitness parameters displayed by the electronic device and in the stored information associated with the current workout compilation. Adjustments to fitness parameters also can be considered data collected about a user's performance of scheduled activities. Thus, the lifestyle companion system can adapt the user's goals, adapt later scheduled activities, and/or suggest activities, references, and/or plug-in modules for the user's consideration based on user-adjustments to the fitness parameters.

Electronic device 1400 also can adjust fitness parameters 1708 and/or a user's fitness goals in real-time based on data collected from sensors 208 of FIG. 2. For example, if the sensor data indicates that the user is in poor physical shape, the electronic device can adjust one or more fitness parameters associated with one or more fitness activities to reduce, for example, the amount of time allocated to the fitness activities and/or the intensity level of the fitness activities. The electronic device also can adjust the user's fitness goals to be less ambitious to maintain the user's motivational level.

In one embodiment of the present invention, electronic device 1400 can adjust fitness parameters 1708 and/or the user's fitness goals based on whether the user's performance metrics indicate that the user is becoming fatigued. For example, electronic device 1400 can detect fatigue by measuring changes in one or more physiological metrics (e.g., breaths per minute, heart rate, or pace) as compared to a predetermined value. Electronic device 1400 also can detect fatigue by measuring changes in one or more physiological metrics as weighted by a weighting factor indicative of an expected intensity of the fitness activity. If the user's physiological metrics indicate fatigue, for example, electronic device 1400 may immediately reduce the intensity of the current fitness activity, e.g., by reducing the number of reps or sets the workout compilation is instructing the user to perform in the present workout.

In another embodiment of the present invention, electronic device 1400 can adjust fitness parameters 1708 and/or the user's fitness goals based on whether the user's performance metrics indicate the user will meet the user's short-term or long-term calorie burning goal. For example, electronic device 1400 can determine the number of calories a user burns by measuring the heat flux radiating from a predetermined location on a person's skin or tracking the amount of movement a user undertakes (e.g., the distance the user runs) with respect to the user's weight. Based on the number of calories burned, the electronic device then can project, for example, whether the user can attain the user's calorie burning goals. If the electronic device determines that the user will not be able to meet his goals, the electronic device can, for example, immediately increase the intensity of the current fitness activity by increasing the number of reps or sets the workout compilation is instructing the user to perform in the present workout.

Additional information about systems and methods for adjusting of user-programmable parameters of a media file (such as the workout compilation of the present invention) during playback of the media file can be found in the incorporated VARIABLE I/O document and the incorporated provisional patent application.

In addition to instructions 1704-1708, interface 1702 also can provide additional visual cues related to the workout compilation, including, e.g., title 1712 of the fitness activity, progress indicator 1714, etc. Progress indicator 1714 can indicate the user's progress through the fitness activities associated with the workout compilation currently being played back by electronic device 1400.

Interface 1702 also can include icon 1716, which closes interface 1702 when actuated by the user. When interface 1702 is closed, electronic device 1400 can return to, for example, interface 1502 of FIG. 15, 1602 of FIG. 16, or 1902 of FIG. 19.

Figure 18:
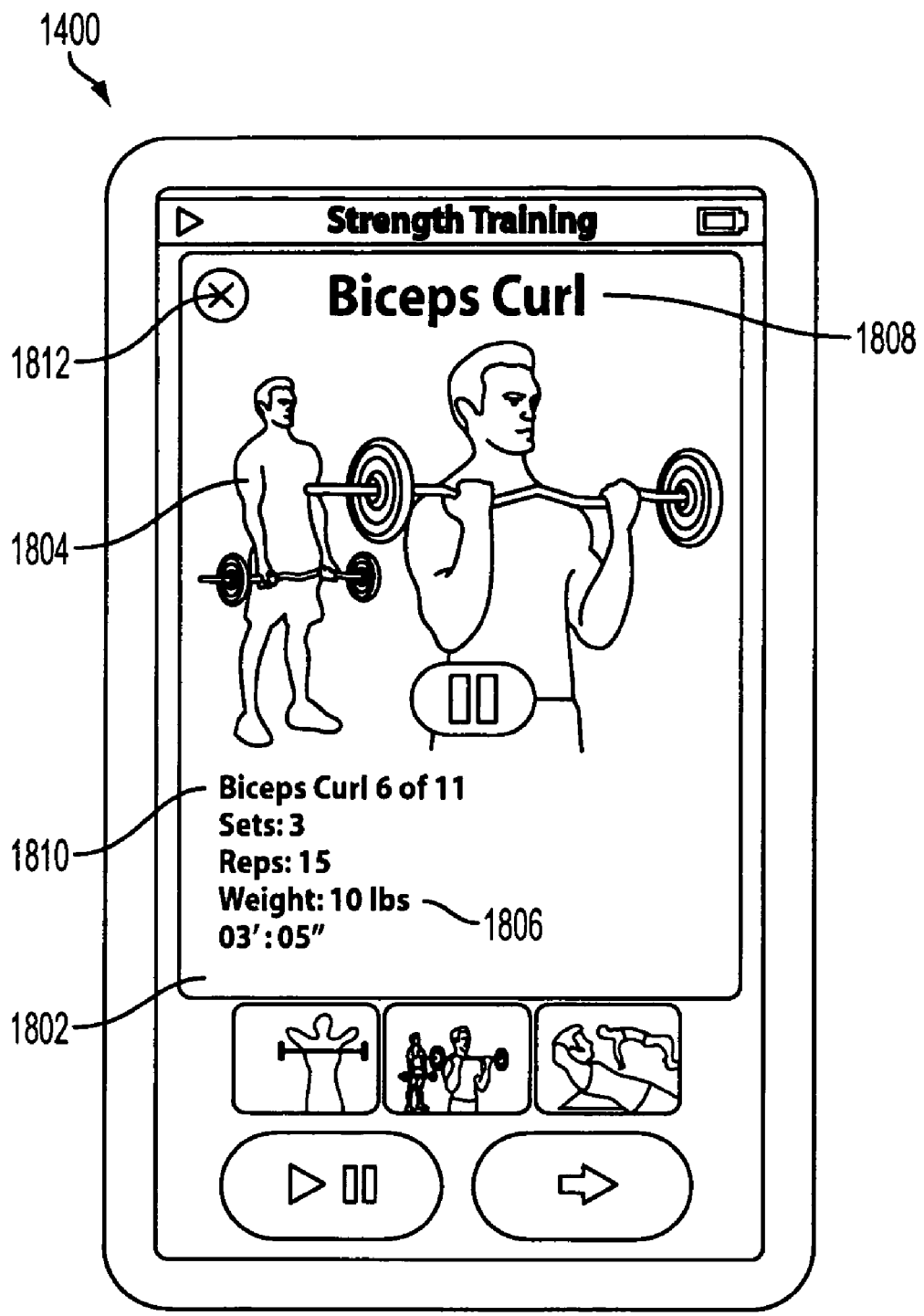

FIG. 18 shows an illustrative graphic user interface provided by electronic device 1400 in accordance with one embodiment of the present invention. Interface 1802 can provide a platform through which the lifestyle companion system can provide the user with more detailed information about a fitness activity. Interface 1802 can be similar to interface 1702 of FIG. 17. For example, interface 1802 also can incorporate pictorial instructions 1804 related to performance of the fitness activity, user-adjustable fitness parameters 1806, title 1808 of the fitness activity, progress indicator 1810, and user-actuable close-interface icon 1812. In one embodiment of the present invention, pictorial instructions 1804 can be larger than that of interface 1702 of FIG. 17. Depending on the area occupied by pictorial instructions 1804, interface may or may not incorporate textual instructions related to performance of the fitness activity.

Figure 19:
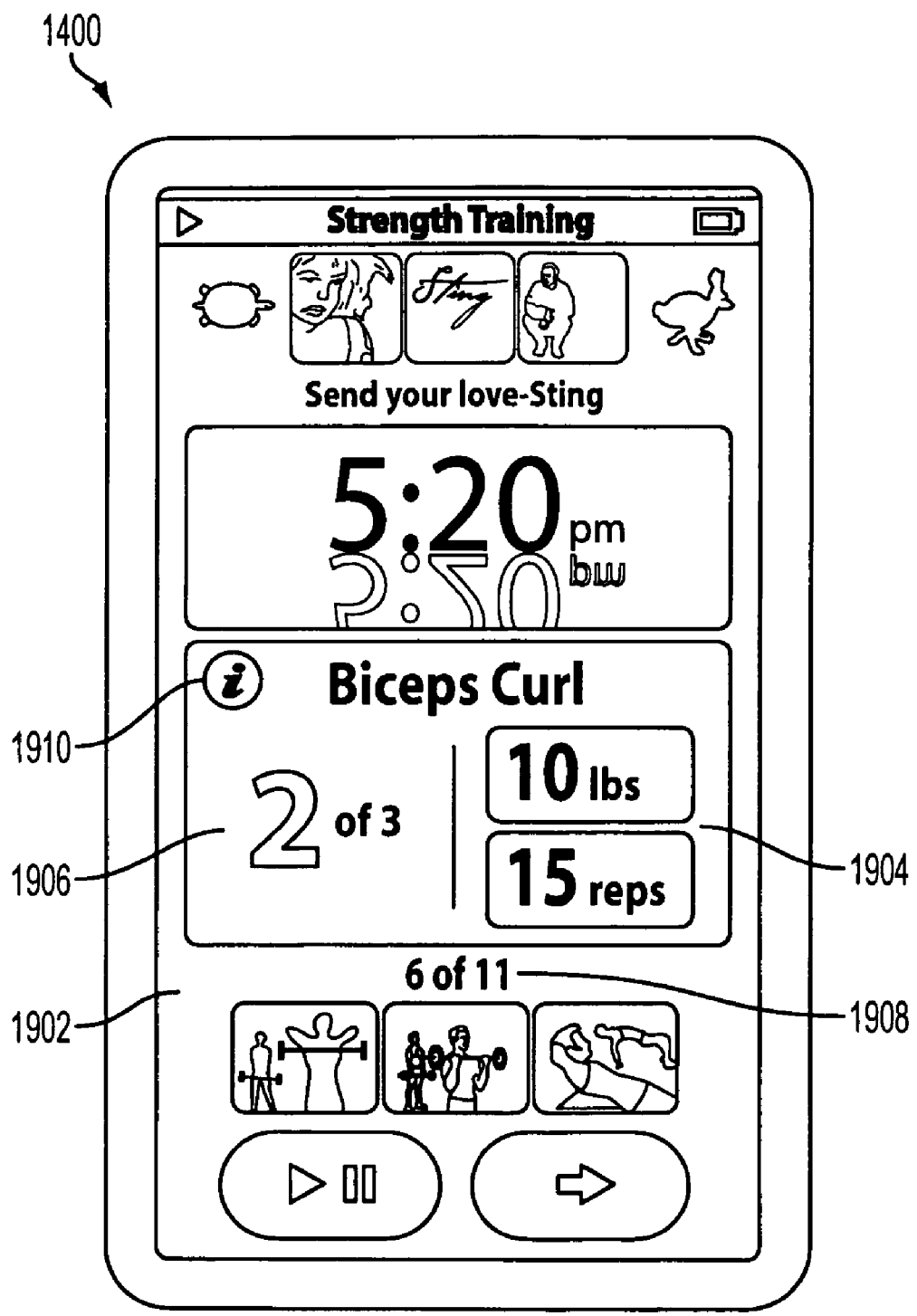

FIG. 19 shows an illustrative graphic user interface provided by electronic device 1400 during one fitness activity in accordance with one embodiment of the present invention. Interface 1902 can incorporate user-adjustable fitness parameters 1904, performance metric 1906, and progress indicator 1908. In one embodiment of the present invention, electronic device 1400 can automatically update performance metric 1906 based on data collected by sensors 208 of FIG. 2. For example, if performance metric 1906 tracks the number of sets completed by the user, electronic device 206 can update the performance metric when the sensor data indicates that the user has completed a set of the prescribed activity.

Interface 1902 also can include user-actuable user input component 1910. When actuated by the user, electronic device 1400 can display information about the current fitness activity, e.g., as described in greater detail above with respect to FIGS. 17 and 18.

Figure 20:
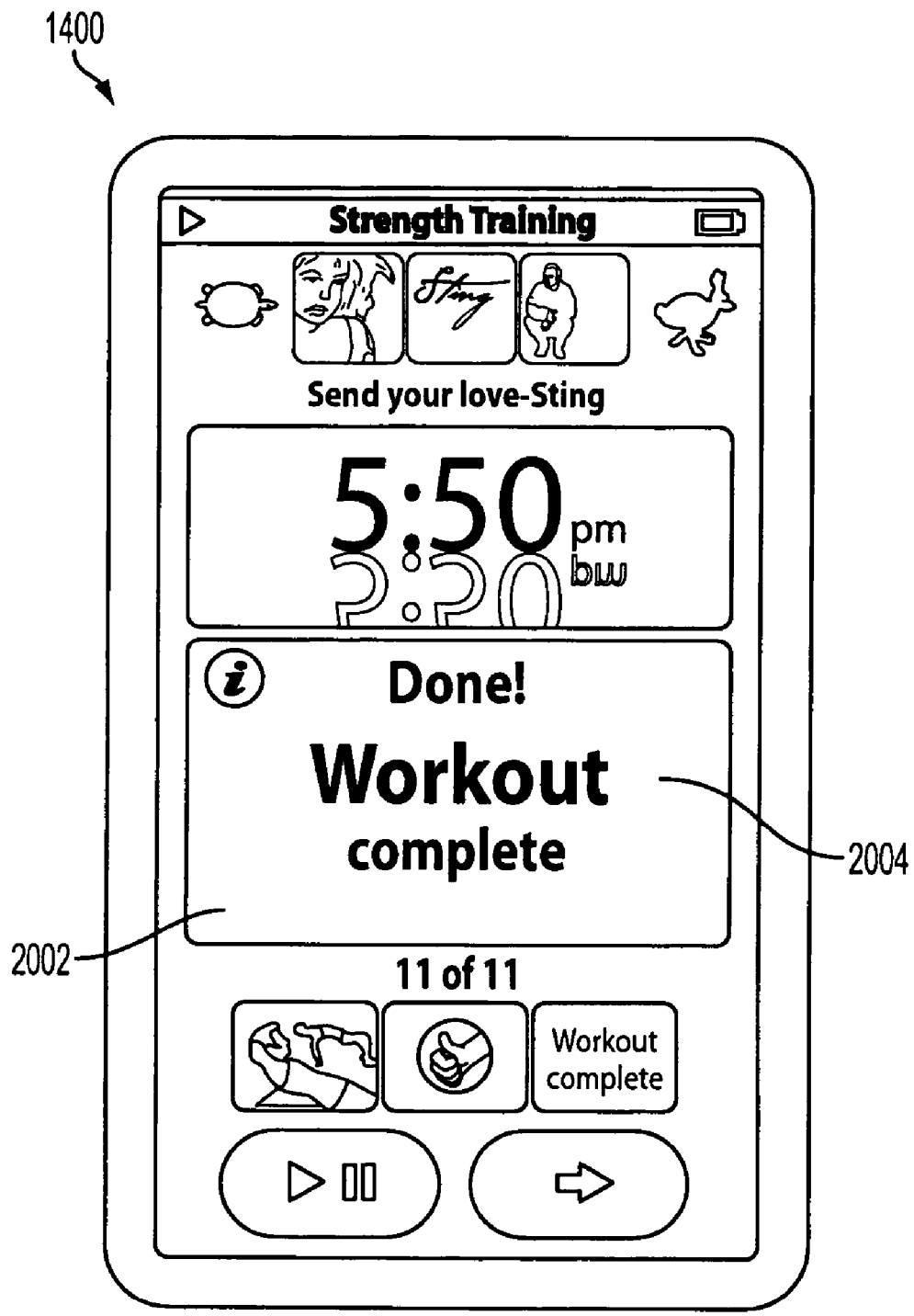

FIG. 20 shows an illustrative graphic user interface of a finish screen on electronic device 1400 in accordance with one embodiment of the present invention. Interface 2002 can be similar to interface 1414 of FIG. 14, except that instructional section 2004 can display a graphic message appropriate for the completion of the workout compilation.

Figure 21:
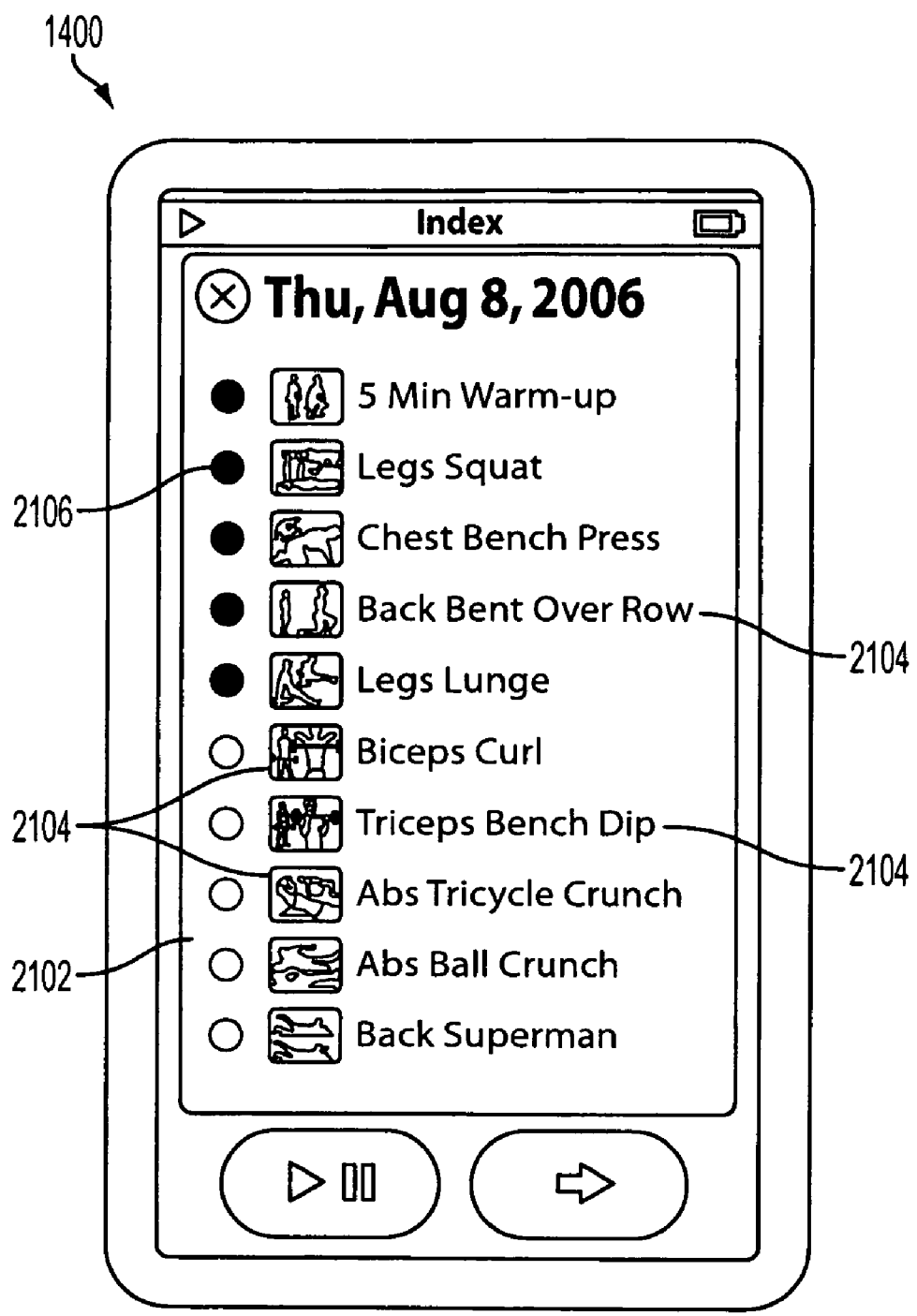

FIG. 21 shows an illustrative graphic user interface of an index of fitness activities associated with a workout compilation in accordance with one embodiment of the present invention. Interface 2102 can provide a platform in which a user can keep track of his progress through a workout compilation. Interface 2102 can incorporate graphic representations 2104 of the fitness activities. The representations can be sorted in the order in which the associated activities are to be performed.

Interface 2102 also can incorporate progress indicator 2106, which can visually distinguish the fitness activities that the user has already performed from the fitness activities that the user has yet to perform. In one embodiment, electronic device 1400 can be configured to determine which activities the user has already performed based on collected sensor data. The electronic device also can be configured to determine which activities the user has already performed based on user input (e.g., user input that indicates the user's desire to advance onto successive activities).

Interface 2102 also can permit a user to jump around to different activities in the workout compilation. For example, if the user has just completed the legs lunge activity and would like to skip to the back superman activity next, the user can indicate this by actuating the graphic representation for the back superman activity. Electronic device 1400 then would advance onto the back superman activity next, rather than the biceps curl activity that originally was scheduled next.

In one embodiment of the present invention, electronic device 1400 can remember the location in the workout compilation at which a user has paused a workout compilation. When a user returns to the paused workout compilation, e.g., after a few minutes, hours, or days, electronic device 1400 can display index interface 2102 to remind the user of his progress through the workout compilation.

In one embodiment of the present invention, electronic device 1400 also can provide audio cues related to the workout compilation and/or a user performance metric. For example, in addition to the visual instructions on instructional section 1420 for initiating the workout, electronic device 1400 also can provide the same instructions audibly. Other audible cues can be related to, for example, the exercise type, the next fitness activity to be performed, the progress of the user through the workout compilation, instructions for a fitness activity (e.g., fitness parameters associated with a fitness activity and/or the proper way to perform a fitness activity), etc. In one embodiment of the present invention, the audio cues can be provided simultaneously with visual cues or in lieu of visual cues.

The audio cues can be provided at predetermined points in the workout compilation (e.g., at the end of each fitness activity) or dynamically provided based on a user's performance metrics. For example, electronic device 1400 can provide audio cues about the user's performance metrics, e.g., in isolation, as compared to the user's long-term or short-term performance goals, and/or as compared to the performance metrics of other people. The audio cues can be motivational in nature. For example, the audio cues can congratulate the user when the user runs her fastest mile or has met a performance goal.

Figure 22:
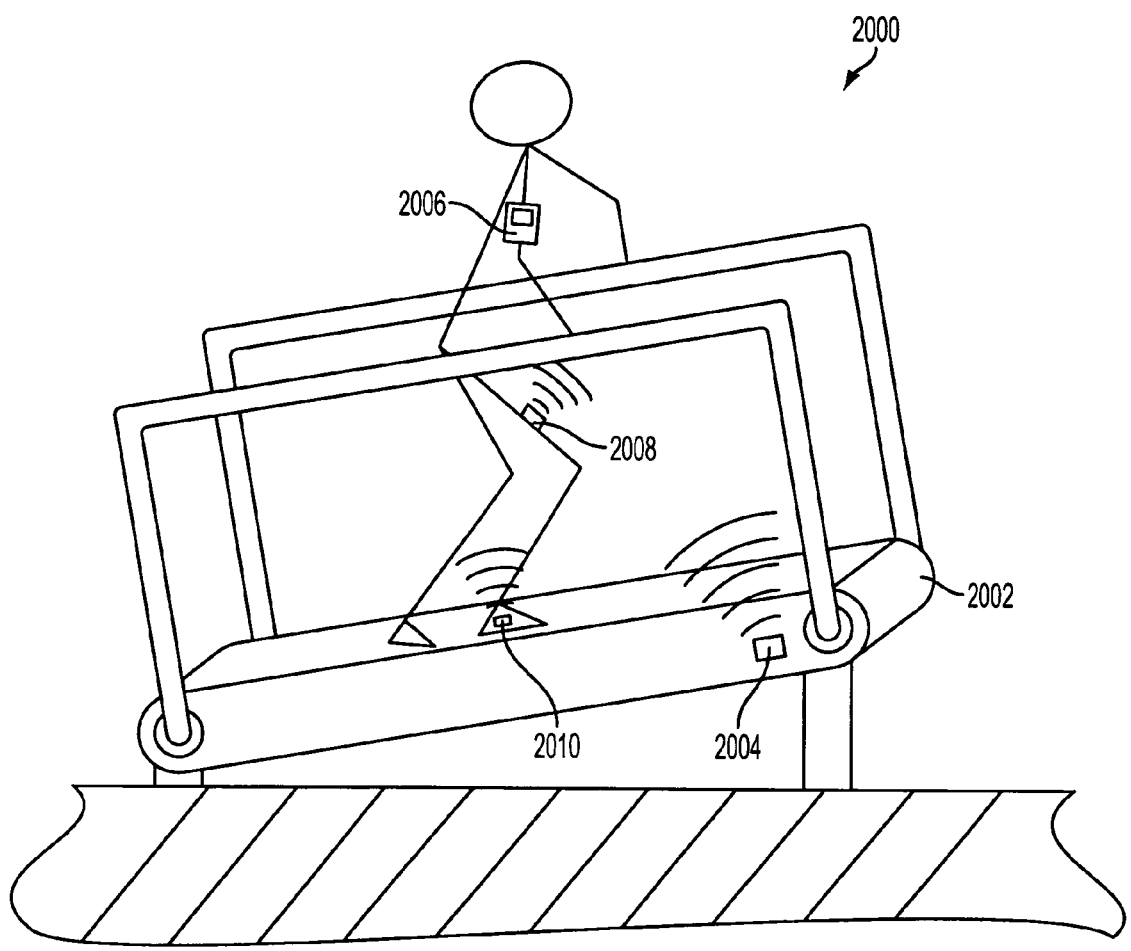
FIG. 22 shows an illustrative fitness system for facilitating collection of data about a user's fitness performance and adaptation of a fitness activity based on the collected data in accordance with one embodiment of the present invention.

FIG. 22 shows an illustrative fitness system for facilitating collection of data about a user's fitness performance and adaptation of a fitness activity based on the collected data in accordance with one embodiment of the present invention. System 2000 can include exercise machine (e.g., treadmill) 2002, integrated exercise machine sensor 2004, portable electronic device 2006 (e.g., iPod™), and wearable sensors 2008 and 2010 (e.g., the sensor from the Nike+iPod Sport Kit and heat flux sensor).

In one embodiment of the present invention, one of the activities of a user's workout compilation can include exercising on exercise machine 2002. Portable electronic device 2006 can collect data from sensors 2004 and 2008-2010 and from other data sources (e.g., manual entry by the user). Based on the collected data and on a user profile stored in memory of the portable electronic device, the portable electronic device can provide media cues to the user and control exercise machine 2002. Portable electronic device 2006 also can store the collected data for future analysis or for transmission to user-authorized entities.

To collect data from the sensors, portable electronic device 2006 can be equipped with a communication module (e.g., communication module 210 of FIG. 2) for receiving signals transmitted by sensors 2004, 2008, 2010 and/or other data sources. If one or more sensors are configured to transmit their data wirelessly, the communication module can be configured to accept the data using the same wireless protocol. If one or more of the sensors (e.g., integrated exercise sensor 2004) are configured to transmit data via a hard-wired connection (e.g., through a dock or cable), the communication module also can be configured to accept the data in the same manner.

Based on the data collected from data sources and the user profile, portable electronic device 2006 can dynamically adapt (in real-time) any of the adjustable fitness parameters of exercise machine 2002 (e.g., speed setting or inclination setting). That is, based on the collected data and the user profile, the portable electronic device can generate control signals to influence operation of the exercise machine. For example, if collected data indicates that the user's heart rate is too high for his weight class, portable electronic device can generate control signals that instruct exercise machine 2002 to immediately reduce its speed and/or reduce its inclination.

The computation for adjusting an exercise parameter of the exercise machine can at least partially be based on comparison of the user's performance metric(s) (e.g., heart rate) to target performance metric(s) (e.g., a target heart rate for the user's weight).

To facilitate communication and other interaction between portable electronic device 2006 and exercise machine 2002, the two devices can undergo a handshaking operation at the start of their interaction. For example, at the beginning of any interaction between the portable electronic device and the exercise machine, exercise machine 2002 can transmit identification data to portable electronic device 2006 to identify the exercise machine. The portable electronic device can use the identification data to determine the proper fitness parameters to adjust. The portable electronic device also can use the identification data to ensure that the collected data is linked with the correct exercise machine when the data is stored in memory. Thus, when the stored data is reviewed later, it can be reviewed in the proper context.

In one embodiment of the present invention, system 2000 can have duplicative data sources. Duplicative data sources can include multiple independent sensors that can provide data about the same performance metric. As used herein, while duplicative data sources can provide data about the same performance metric, duplicative data sources also can provide data about different performance metrics.

One advantage of using duplicative data sources to track a user's performance of an activity is the opportunity to select and use data from the data source providing the more accurate data. For example, a treadmill can provide calorie count based on the weight of the user and the miles the user has traversed. However, portable electronic device 2006 also can receive calorie information from a heat flux sensor (e.g., sensor 2008) that measures heat radiating from the user. Under some circumstances, heat flux information may be a more accurate indication of calories burned than the treadmill information. In one embodiment of the present invention, system 2000 can determine the duplicative data source providing the more accurate information by comparing data from each duplicative data source to the user's historic data and/or to a reference or calibration value or range of values. Thus, the present invention can include the ability to manually or automatically select among two or more data sources. Other embodiments of the present invention described herein also can include duplicative data sources.

While FIG. 22 illustrates a treadmill for use with the lifestyle companion system of the present invention, other exercise machines having adjustable exercise parameters also may be equipped to communicate with portable electronic device 2006 in the manner described. For example, adjustable weight machines, adjustable elliptical trainers, adjustable rowers, adjustable stationary bicycles, or any other suitable exercise machine can be equipped to communicate with (e.g., be controlled by and provide data to) portable electronic device 2006.

In one embodiment of the present invention, multiple exercise machines in a fitness facility can be equipped to communicate with portable electronic devices 2006. This can permit a user to aggregate his performance metrics from multiple exercise machines onto a single device (e.g., portable electronic device 2006). For example, the user can collect and store data from multiple exercise machines during a single workout or multiple workouts using portable electronic device 2006. Advantageously, rather than aggregating and analyzing data about the user's performance metrics in a piecemeal fashion, the user or an authorized entity can efficiently obtain a more complete picture of the user's performance and fitness abilities using the present invention.

Portable electronic device 2006 can provide audio and visual cues based on the data collected from sensors that track the user's performance and from sensors that track other people's performance(s) in accordance with the principles of the present invention. For example, a user and his workout partner may be jogging together, exercising on separate exercise machines, or otherwise working out together. A user's portable electronic device can be configured to accept data indicative of his own performance metrics from sensors associated with his own user profile (or portable electronic device) and data indicative of his partner's performance metrics. The data indicative of the user's partner's performance metrics can be transmitted from the partner's portable electronic device or from sensors associated with the partner's user profile or portable electronic device.

The user's electronic device may compare the partner's performance metrics to that of his own, and, based thereon, provide the user with a media cue. In one embodiment, the media cues can be indicative of the user's performance metrics and/or the partner's performance metrics. For example, if the user's performance metrics do not compare favorable with the partner's performance metrics, the user's portable electronic device can instruct the user to "Speed it up. Partner has already run 3 miles and you have only run 2 miles!"

In an alternative example, the user and his exercise partner may be exercising on different types of exercise machines equipped to communicate with portable electronic devices 2006. The user's electronic device and the partner's electronic device can each log the performance metrics of each person. The partner's electronic device can send the partner's performance metrics to the user's electronic device. The user's electronic device then can compare the user's performance metrics to those of the partner with respect to, for example, calories burned. After a predetermined period of time, the user's electronic device can instruct the user to "Speed it up. You have burned 50 calories in 20 minutes, while your partner has burned 70 calories in 20 minutes."

Figure 23A:
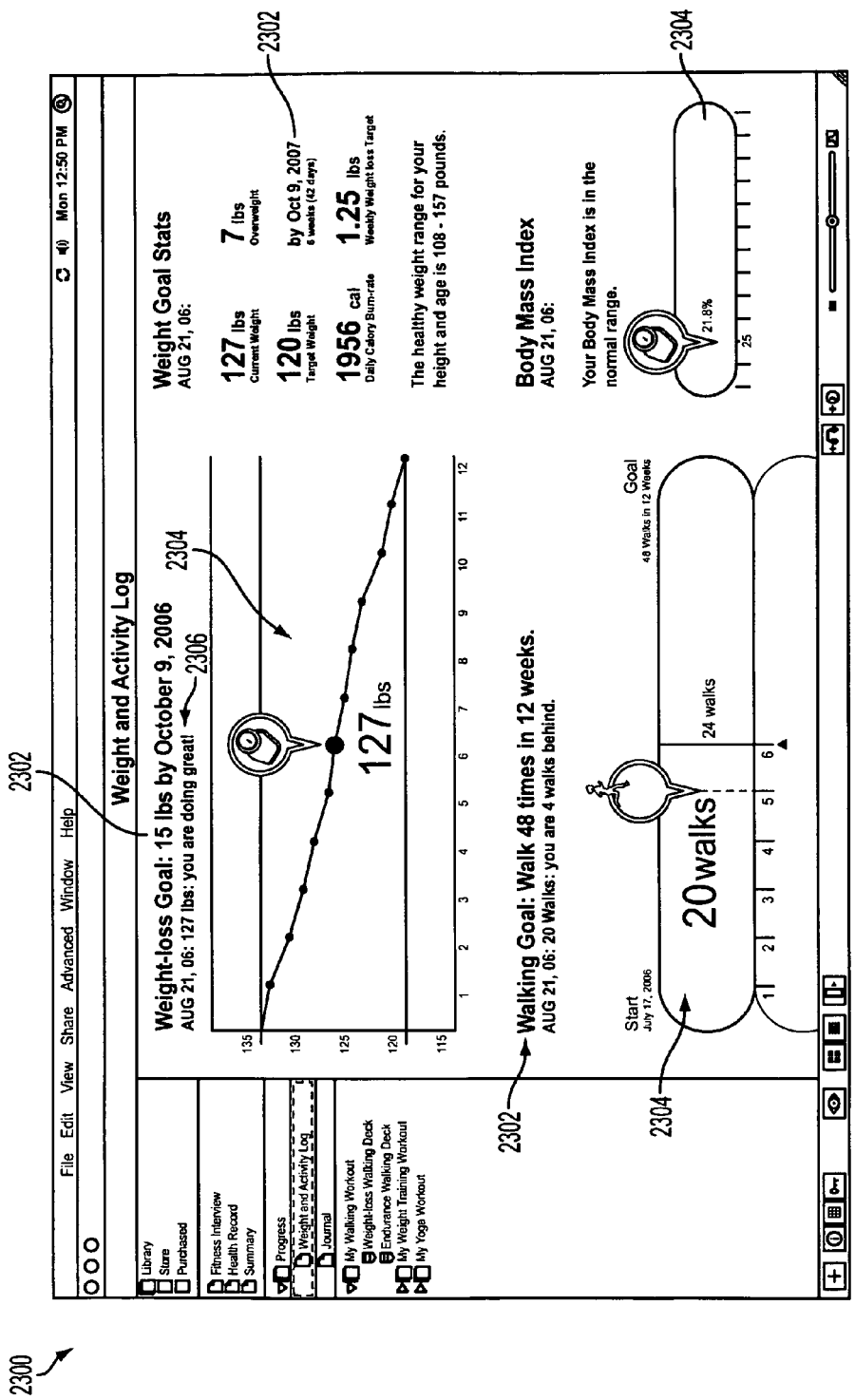
FIG. 23A shows an illustrative progress report in accordance with one embodiment of the present invention.

FIG. 23A shows an illustrative progress report in accordance with one embodiment of the present invention. Progress screen 2300 can include textual indications 2302 and pictorial indications 2304 of a user's progress towards fitness goals. Progress screen 2300 also can incorporate motivational messages 2306 tailored to the user's performance metrics (e.g., as compared with the target metrics). For example, in the embodiment shown in FIG. 23A, screen 2300 displays the following motivational message: "You are doing great!" Progress toward other fitness goals or lifestyle goals also can be shown in graphical interfaces (e.g., similar to screen 2300) without departing from the spirit of the invention.

Figure 23B:
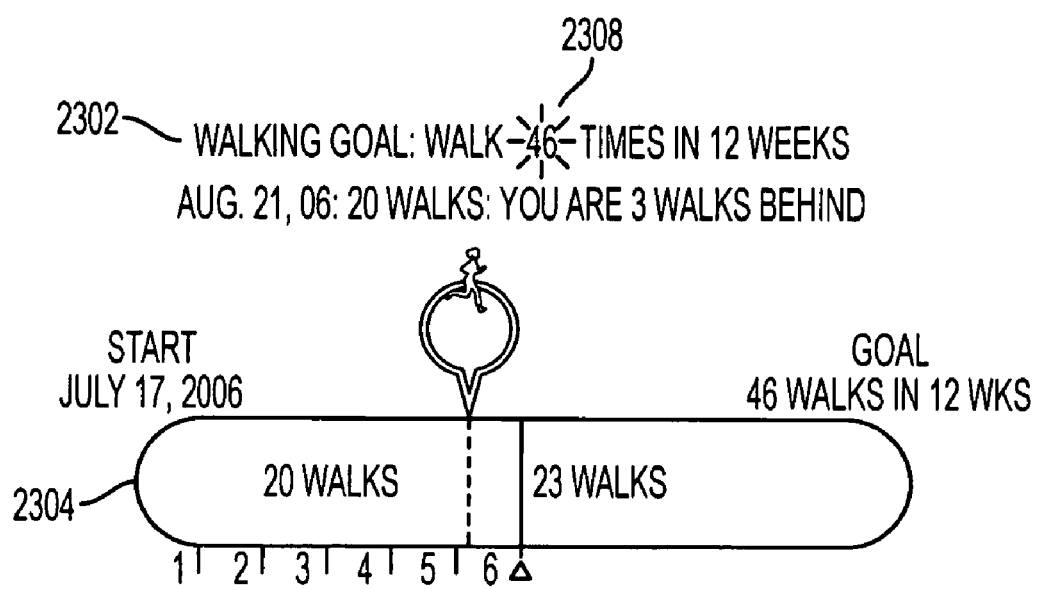
FIG. 23B shows a portion of the illustrative progress report of FIG. 23A after it is adapted based on the user's performance metrics in accordance with one embodiment of the present invention.

FIG. 23B shows illustrative progress report 2300 after goal adaptation based on the user's performance metrics in accordance with one embodiment of the present invention. For example, textual indication 2302 and pictorial indication 2304 can be updated to show a decrease in the total number of walks the user has to perform over a predetermined period as compared to the original goal. In one embodiment of the present invention, the adjustment can be visually distinguished, e.g., as blinking graphic 2308. The adjustment can be implemented in response to the user's performance metrics, as determined from data collected from data sources, e.g., sensors 208 of FIG. 2. For example, the target number of walks can be reduced as a result of the user's poor performance through a first predetermined time period (e.g., four weeks) of the fitness schedule.

In accordance with another embodiment, the lifestyle companion system of the present invention can facilitate synchronous group activities. For example, the lifestyle companion system can be used to ensure that each participant in a group activity is being instructed to perform activities in concert with the other participants of the activity. That is, each participant can be instructed to perform the same activities as the other participants (e.g., in group workouts) or activities that complement the activities the other participants are being instructed to perform (e.g., in a band, theatrical production, or interactive sport activity).

Figure 24:
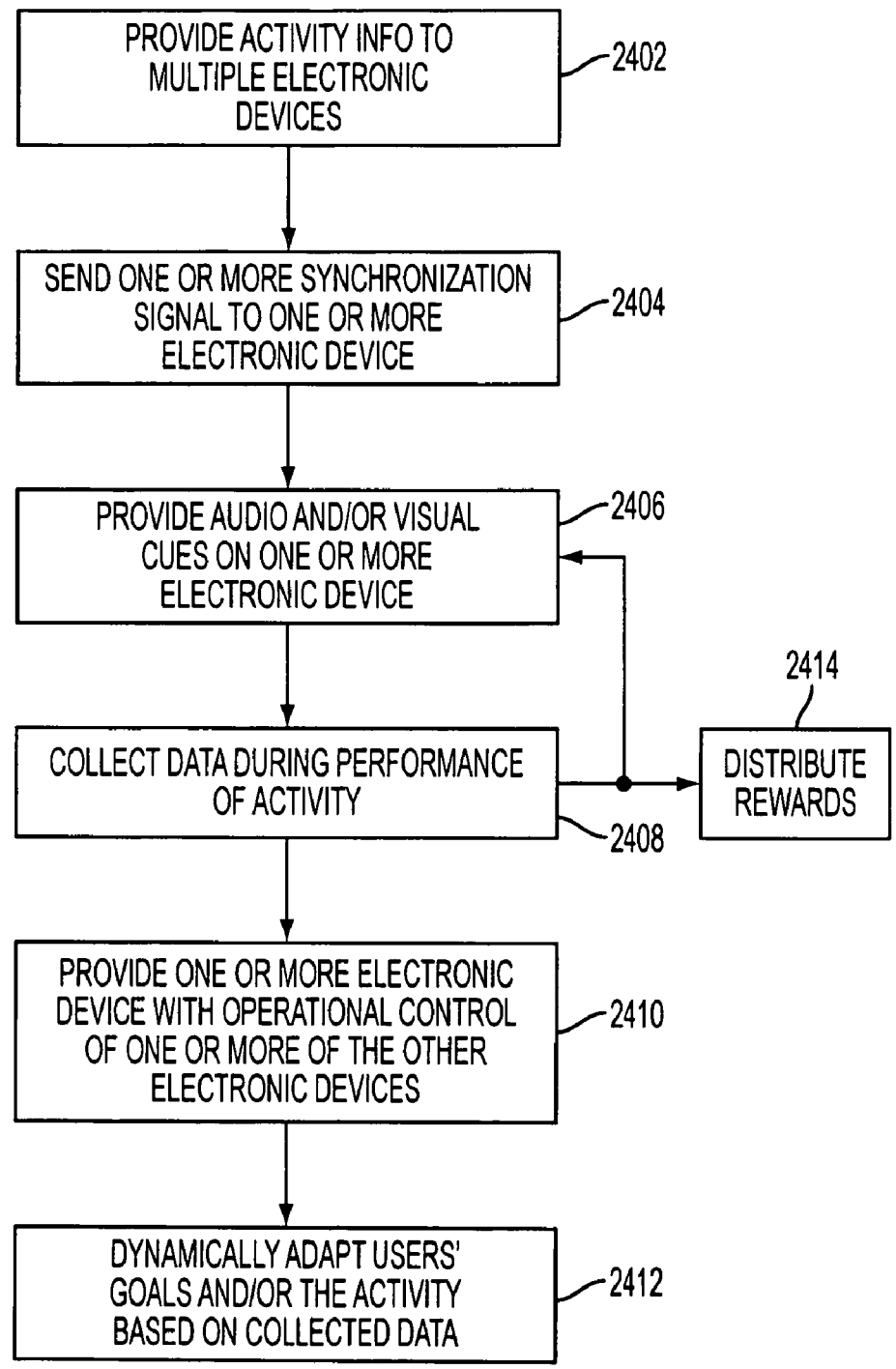
FIG. 24 shows an illustrative flow chart for facilitating synchronous group activities in accordance with one embodiment of the present invention.

FIG. 24 shows an illustrative flowchart for facilitating synchronous group activities in accordance with one embodiment of the present invention. In step 2402, the lifestyle companion system can transmit activity files to multiple member electronic devices to be used by the members of the group. The activity files can be downloaded onto each member electronic device (e.g., a portable media device similar to the iPod™) from a local server, a central server, or a participating electronic device (e.g., a master electronic device). In one embodiment of the present invention, the activity file can be created by a group organizer (e.g., fitness trainer, band leader, drill sergeant, theatrical director, athletic coach, etc.) in accordance with the systems and methods described herein.

In one embodiment of the present invention, the same activity file (e.g., a workout compilation) can be downloaded to all of the member devices. Alternatively, each member electronic device can be provided with different activity files. For example, the activity files can be different because the activity files may store different media items corresponding to different but complementary activities. When the activity files are played back on the member devices, the different activity files can instruct each group participant to perform at least one activity that is different than an activity another group participant is being directed to perform (e.g., in a band, theatrical production, or interactive sport activity). Alternatively, the activity files can be different because the activity files may store different parameters associated with the same activities. When the activity files are played back on the member devices, the activity files can instruct the group participants to perform the same activity, but in accordance with different parameters (e.g., different weights in a bicep curl activity).

In one embodiment of the present invention, an activity file can include a file in which all media items and parameters associated with an activity or compilation of activities are stored. Alternatively, an activity file can include multiple files in which all media items and parameters associated with an activity or compilation of activities are stored. For example, an activity file can include a first file in which the media items are stored and a second file in which the parameters are stored. Activity files can be considered different when they share the same media items but different parameters.

Once the activity file has been downloaded into each participating electronic device, the group members can begin performing the activity. In step 2404, one or more member electronic devices can send one or more synchronization signals to one or more of the other member electronic devices via wired or wireless communication protocols. For example, a master electronic device (e.g., used by the group organizer) can send out a synchronization signal to the other electronic devices to indicate that each device should begin playback of the downloaded activity file. During subsequent playback of the activity file, the master electronic device can continue to periodically send synchronization pulses to the other member devices to ensure that each member electronic device continues to play back the downloaded activity file in concert with the other member electronic devices.

In step 2406, each member electronic device can provide audio and/or visual cues to their respective participants in accordance with the systems and methods described herein. The audio and/or visual cues provided by each member device can be the same as those provided to the other members. Alternatively, the audio and/or visual cues provided by one or more of the member devices can be different than those provided to the other members. For example, when two or more participants are instructed to perform different but complementary activities (e.g., in a band, theatrical production, or interactive sport activity), each participant's electronic device can provide audio and/or visual cues that are appropriate for the activity that participant is being instructed to perform.

In one embodiment, the media cues can be related to data collected in step 2408. For example, the portable electronic devices can collect data indicative of the users' performance metrics before the devices provide media cues related thereto. The media cues also can be related to a member's performance as compared to the performance of one or more other members (as discussed above with respect to FIG. 22). For example, a first member device can receive data indicative of performance metrics of first and second members of the group activity. The first member device can compare the two sets of data and transmit a media cue to the first member based on the comparison.

In one embodiment of the present invention, the audio and/or visual cues related to the group activity can be blended or overlaid with entertainment media tracks that each participant has selected for playback on their respective electronic device. For example, each participant may choose to play different music while working out to a group fitness activity.

The present invention can blend audio cues for the group fitness activity into the different music being played on each member electronic device.

In step 2408, the lifestyle companion system can collect data about the performance of the group participants. For example, each participating device can collect data from sensors associated therewith in accordance with the systems and methods described herein. The participating devices also can transmit the sensor data to other participating devices, such as the master device and/or another member device. Alternatively, the master device can be configured to accept the sensor data from the sensors directly without having to wait for transmission from another participating device.

In step 2410, one or more participating electronic devices (including a master electronic device) can be provided with at least partial operational control of one or more of the other member electronic devices. For example, a master electronic device can be provided with the ability to dynamically adjust parameters of the activity as discussed in greater detail below with respect to step 2412. Alternatively, each participating electronic device can have the ability to generate and send control signals to influence operation of the other participating electronic devices and/or the master device. The control signals can, for example, pause playback of the activity file or temporarily reduce the volume on the other electronic device(s) in the group. For example, when one person wants to communicate with the other person(s) in the group activity, the participating electronic devices can have the ability to lower the volume on or pause the other electronic device(s), e.g., in response to speech or activation of a user input by the first group member.

In step 2412, the lifestyle companion system can permit a member's own electronic device and/or a master electronic device to dynamically adapt one or more of the user's goals based on the data collected in step 2408. The lifestyle companion system also can permit a member's own electronic device and/or a master electronic device to dynamically adapt the parameters of the current activity based on the collected data. For example, a master electronic device can be configured to adapt a user's goals or the parameters of an activity on one or more of the participating electronic devices by generating and transmitting control signals to the target electronic device over a wireless or wired link, even while the participating electronic devices are playing the currently loaded activity file. The control signals can influence operation of the recipient electronic device by, for example, changing the parameters of the activities stored in the activities files on those electronic devices.

In step 2414, the lifestyle companion system can distribute rewards to the users, as described, for example, in the incorporated REWARDS SYSTEMS document and the incorporated provisional patent application.

Figure 25:
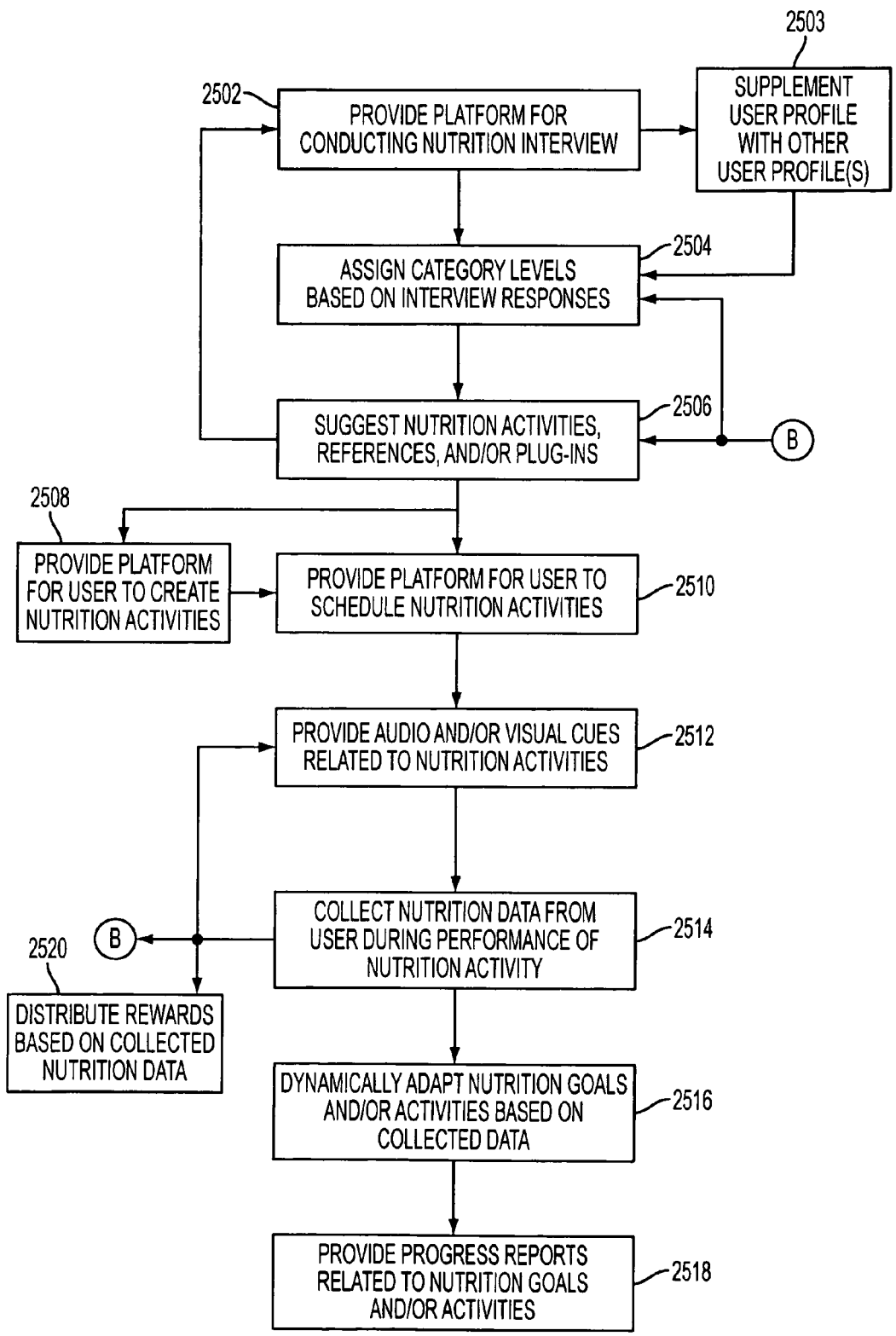
FIG. 25 shows an illustrative flow chart for implementing a nutrition program with the lifestyle companion system in accordance with one embodiment of the present invention.

FIG. 25 shows an illustrative flow chart for implementing a nutrition program with the lifestyle companion system in accordance with one embodiment of the present invention. In step 2502, the lifestyle companion system can provide a platform for conducting an interview related to nutrition. Interview questions can be directed to, e.g., weight-loss goals, the user's current diet, food allergies, food preferences, medical conditions, medications, financial allocation for nutritional needs, religion, time available to prepare food, other lifestyle information, etc. Based on the user interview responses, the lifestyle companion system can generate a user nutritional profile to which the lifestyle companion system can later refer in steps 2504-2506 and 2516-2520.

In step 2503, the lifestyle companion system can supplement the user's profile with the profiles of dining partners so that the lifestyle companion system can suggest, for example, nutritional activities (e.g., recipes, restaurants, etc.) that are appropriate for the user and his dining partners.

In step 2504, the lifestyle companion system can assign nutritional category levels based on the user's interview responses. For example, users may be labeled as vegan, vegetarian, kosher, lactose intolerant, dieter, etc.

In step 2506, the lifestyle companion system can suggest nutrition activities, references, and/or plug-in modules based directly or indirectly on the user's interview responses. For example, the lifestyle companion system can recommend the user patronize certain restaurants in the area's hometown. In one embodiment of the present invention, the lifestyle companion system can be linked to the menus of restaurants and the lifestyle companion system can suggest menu selections based, for example, on the user's nutritional needs and restrictions and/or on the user's availability of funds.

In one embodiment of the present invention, a user can be provided with a portable electronic device on which is stored his user nutrition profile. The user can be dining at a suggested restaurant and desire the lifestyle companion system to suggest menu selections based on his dietary and financial restrictions. If the user's portable electronic device already has the restaurant's menu stored in its memory, the user's device can immediately cross-reference the user's profile with the menu to select appropriate menu selections. However, if the user's portable electronic device does not have the restaurant's menu stored in its memory, the user can download the menu by linking his device to the restaurant's server. This can be accomplished, for example, by coupling the communication module on the user's device to an internet link or a dock coupled to the restaurant's server. Once the restaurant's menu is downloaded into the user's device, the device can select the appropriate menu selections. The user's device can provide the suggestions audibly and/or through graphics (e.g., text, still images, and/or video) on a display.

The lifestyle companion system also can suggest recipes and/or meal plans tailored to the needs of the user. The recipes and meal plans can be suggested based on the user's nutritional needs and/or restrictions, any specific diets the user is trying, relevant life events (e.g., a user's birthday and/or the user's exercise schedule), etc. In one embodiment of the present invention, the system can receive input from local food providers (e.g., grocery stores). Thus, the recipes and meal plans suggested by the lifestyle companion system also can be influenced by a variation of prices at the local food providers.

The lifestyle companion system also can suggest websites or plug-in modules for special diet plans, e.g., diet plans branded by Jenny Craig or Weight Watchers. The lifestyle companion system can be pre-loaded with plug-in modules related to nutrition or the user can download nutrition plug-in modules from a database of such offerings, e.g., from iTunes™.

In step 2508, the lifestyle companion system can provide a platform for the user to create nutrition activities. For example, the lifestyle companion system can provide an interface similar to interface 1200 of FIG. 12 for the user to plan meals or customize meal plans suggested by the lifestyle companion system in step 2506. However, rather than building blocks of fitness activities, the nutrition interface can offer building blocks of recipes or food dishes sorted, for example, by the food groups and/or courses (e.g. appetizer, entrée, or dessert).

In step 2510, the lifestyle companion system can provide a platform for the user to schedule nutrition activities. For example, the user can schedule shopping trips to local food providers identified with respect to the recipes suggested in step 2506. The user also can schedule dining out opportunities at the restaurants suggested in step 2506.

In step 2512, the lifestyle companion system can provide audio and/or visual cues related to the nutritional activities. For example, the lifestyle companion system can provide nutritional information about a selected restaurant and/or menu selection. The lifestyle companion system also can indicate how the menu selections affect the user's nutritional plan and/or goals.

Another example of a visual cue can include graphic indications of suggested portion size. For example, if a recipe or diet plan calls for a certain portion of an ingredient or food, the lifestyle companion system can provide visual comparisons of the suggested portion size to an everyday object. Illustratively, if a recipe or meal plan calls for a cup of broccoli, the lifestyle companion system can graphically indicate that a cup of broccoli may have a size comparable to a baseball.

In step 2514, the lifestyle companion system can collect data about the user's performance of an activity. For example, the user can carry a portable electronic device having a scanner that can scan a barcode representing the food purchased and/or eaten by the user. Alternatively, the user can couple his portable electronic device into a dock at a restaurant. A server at the restaurant then can download nutritional information about the user's meal into the user's device.

In step 2516, the lifestyle companion system can dynamically adapt the user's nutritional goals and/or activities based on the data collected in step 2514. For example, if a user consumes too many calories, the lifestyle companion system can reduce the user's future allotment of calories by, for example, suggesting different recipes or menu selections in step 2506, suggesting different portions in steps 2506 and 2512, and/or changing the ingredients in suggested recipes. The lifestyle companion system also can adjust the user's nutritional goals if data collected over a predetermined period of time indicate that the user's nutritional habits will not enable the user to reach the user's nutritional goals.

In step 2518, the lifestyle companion system can provide progress reports related to the user's nutritional habits, goals, and/or activities.

In step 2520, the lifestyle companion system can distribute rewards to the user based on nutrition data collected in step 2514, as described, for example, in the incorporated REWARDS SYSTEMS document and the incorporated provisional patent application.

Although particular embodiments of the present invention have been described above in detail, it will be understood that this description is merely for purposes of illustration. Alternative embodiments of those described hereinabove also are within the scope of the present invention. For example, alternative embodiments of the present invention can incorporate any one or more of the steps described with respect to FIGS. 1, 24, and 25. For example, in one embodiment of the present invention, the lifestyle companion system can permit a user to compile and play back a compilation of activities without the user having to go through an interview and/or without collected data about the user's activities. Also, alternative embodiments of the present invention also can provide any one or more of the screens and user interfaces described herein.

Furthermore, various embodiments described herein or portions thereof can be combined without departing from the present invention. For example, fitness partners can use the lifestyle companion software described with respect to FIGS. 12-13 to compose separate workout compilations customized for each individual, use their respective portable electronic devices to control and collect data from exercise machines as described with respect to FIG. 22, and use their respective portable electronic devices to influence operation of each other's portable electronic device as described with respect to FIG. 24.

The above described embodiments of the present invention are presented for purposes of illustration and not of limitation, and the present invention is limited only by the claims which follow.

What is claimed is:

1. A portable electronic device comprising:
   a display;
   memory for storing information about multiple activities;
   a communication module for accepting sensor data indicative of a user's performance metrics; and
   a controller configured to provide a filmstrip of graphics and a visual representation of entertainment media simultaneously on the display, wherein the filmstrip of graphics is related to at least a current activity and a first future activity, wherein the entertainment media is associated with at least one of the current activity and the first future activity, wherein the controller is configured to generate the graphics based on the information stored in the memory and to update the filmstrip based on data informative of advancement from the current activity to the first future activity, and wherein the visual representation is an entertainment filmstrip comprising:
   a graphic representation of a first entertainment media file associated with the current activity; and
   a graphic representation of a second entertainment media file associated with the first future activity.

2. The portable electronic device of claim 1, wherein the controller is configured to provide an index of graphics and a progress indicator on the display, wherein:
   the graphics of the index represent activities for which information is stored in the memory; and
   the progress indicator visually distinguishes activities that the user already has performed from activities that the user has yet to perform.

3. The portable electronic device of claim 2, wherein the controller is configured to determine which activities the user has performed based on the sensor data.

4. The portable electronic device of claim 1, wherein the controller is configured to update the filmstrip based on sensor data indicative of the user's completion of the current activity.

5. The portable electronic device of claim 1, wherein the controller is configured to update the filmstrip based on user input data.

6. The portable electronic device of claim 1, wherein the controller is configured to provide instructions related to the current activity on the display, wherein the instructions are a part of the information stored in the memory.

7. The portable electronic device of claim 6, wherein the controller is configured to update the instructions to relate to the first future activity based on data that indicates the user has completed performance of the current activity.

8. The portable electronic device of claim 1, wherein the controller is configured to update the filmstrip by adding a graphic related to a second future activity, wherein the graphic is generated based on the information stored in the memory.

9. The portable electronic device of claim 1, wherein the graphics comprises:
   a graphic representation of the current activity; and at least one of a graphic representation of the first future activity and a graphic representation of a first previous activity.

10. The portable electronic device of claim 1, wherein the controller is configured to update the filmstrip by at least one of:
adding a graphic representation of a second future activity to the filmstrip; and
removing a graphic representation of a previous activity from the filmstrip.

11. The portable electronic device of claim 1, wherein the entertainment media comprises at least the first entertainment media file that is associated with at least the current activity.

12. The portable electronic device of claim 11, wherein the first entertainment media file is stored in the memory.

13. The portable electronic device of claim 11, wherein the controller is configured to accept user input for associating the first entertainment media file with the current activity.

14. The portable electronic device of claim 11, wherein the first entertainment media file is associated with the current activity based on the energy rank of the first entertainment media file and the expected intensity of the current activity.

15. The portable electronic device of claim 14, wherein the energy rank of the first entertainment media file is based on the tempo of the first entertainment media file.

16. The portable electronic device of claim 11, wherein the first entertainment media file comprises one of a music file and a video file.

17. The portable electronic device of claim 11, wherein the graphic representation of the first entertainment media file comprises at least one of text and a still image that identifies the contents of the first entertainment media file.

18. The portable electronic device of claim 11, wherein the controller is configured to playback the first entertainment media file when the controller simultaneously provides the filmstrip and the visual representation.

19. The portable electronic device of claim 11, wherein:
a plurality of entertainment media files comprising the first entertainment media file are accessible by the controller;
each entertainment media file of the plurality of entertainment media files comprises an energy rank; and
the controller is configured to select the first entertainment media file from the plurality of entertainment media files for association with the current activity based on the energy rank of the first entertainment media file and the expected intensity of the current activity.

20. The portable electronic device of claim 1, wherein the controller is configured to update the visual representation based on the data informative of advancement from the current activity to the first future activity by at least one of:
adding a graphic representation of a third entertainment media file associated with a second future activity to the visual representation; and
removing a graphic representation of a fourth entertainment media file associated with a previous activity from the visual representation.

21. The portable electronic device of claim 1, wherein the entertainment media comprises a playlist of a plurality of entertainment media files that is associated with at least the current activity.

22. The portable electronic device of claim 1, wherein:
the entertainment media comprises the first entertainment media file that is associated with the current activity and the second entertainment media file that is associated with the first future activity; and the controller is configured to update the visual representation of the entertainment media based on the data informative of advancement from the current activity to the first future activity.

23. A method for guiding a user of an electronic device through a compilation of activities comprising at least a first activity and a second activity, the method comprising:
accessing a first graphic related to the first activity in the compilation;
accessing a second graphic related to the second activity in the compilation;
accessing a visual representation of at least a first entertainment media file that is associated with the compilation;
simultaneously displaying on a display of the portable electronic device:
an activity filmstrip comprising at least the first graphic and the second graphic; and
the visual representation;
accepting input to the portable electronic device informative of advancement from the first activity of the compilation to the second activity of the compilation; and
updating the activity filmstrip in response to the accepted input, wherein the updating the activity filmstrip comprises at least one of:
adding to the activity filmstrip a graphic related to an activity that follows the second activity in the compilation; and
removing from the activity filmstrip a graphic related to an activity that precedes the second activity in the compilation, wherein the visual representation is an entertainment filmstrip comprising:
a first entertainment graphical representation of the first entertainment media file that is associated with the first activity; and
a second entertainment graphical representation of a second entertainment media file that is associated with the second activity.

24. The method of claim 23 further comprising playing back the first entertainment media file simultaneously with the displaying.

25. The method of claim 23 further comprising updating the entertainment filmstrip in response to the accepted input.

26. The method of claim 25, wherein the updating the entertainment filmstrip comprises at least one of:
adding to the entertainment filmstrip a graphical representation of an entertainment media file that is associated with the activity that follows the second activity in the compilation; and
removing from the entertainment filmstrip a graphical representation of an entertainment media file that is associated with the activity that precedes the second activity in the compilation.

27. The method of claim 23, wherein the input comprises sensor data indicative of the user's completion of the first activity.

28. An electronic device for guiding a user through a compilation of activities comprising at least a first activity and a second activity, the device comprising:
a display; and
a controller configured to:
access a first instructional graphic related to the performance of the first activity;
access a second instructional graphic related to the performance of the second activity;
access a visual representation of at least a first entertainment media file associated with the compilation;

simultaneously display on the display:
   an activity filmstrip comprising at least the first instructional graphic and the second instructional graphic; and
   the visual representation;
accept an input to the electronic device informative of advancement from the first activity of the compilation to the second activity of the compilation; and
update the activity filmstrip in response to the input by at least one of:
   adding to the activity filmstrip a graphic related to an activity that follows the second activity in the compilation; and
   removing from the activity filmstrip a graphic related to an activity that precedes the second activity in the compilation, wherein the visual representation is an entertainment filmstrip comprising:
      a first entertainment graphical representation of the first entertainment media file that is associated with the first activity; and
      a second entertainment graphical representation of a second entertainment media file that is associated with the second activity.

29. The electronic device of claim 28, wherein the controller is further configured to play back the first entertainment media file simultaneously with the displaying.

30. The electronic device of claim 28, wherein the controller is further configured to update the entertainment filmstrip in response to the accepted input.

31. The electronic device of claim 30, wherein the controller is configured to update the entertainment filmstrip by at least one of:
   adding to the entertainment filmstrip a graphical representation of an entertainment media file that is associated with the activity that follows the second activity in the compilation; and
   removing from the entertainment filmstrip a graphical representation of an entertainment media file that is associated with the activity that precedes the second activity in the compilation.

32. The electronic device of claim 28, wherein the input comprises sensor data indicative of the user's completion of the first activity.

* * * * *